(12) United States Patent
Okada et al.

(10) Patent No.: US 10,640,456 B2
(45) Date of Patent: May 5, 2020

(54) COMPOUND AND INTERMEDIATE THEREOF

(71) Applicants: DAI NIPPON PRINTING CO., LTD., Tokyo-to (JP); YAMAMOTO CHEMICALS, INC., Yao-shi, Osaka (JP)

(72) Inventors: Masato Okada, Tokyo-to (JP); Takafumi Yoshida, Yao (JP); Satoshi Kinoshita, Yao (JP)

(73) Assignees: DAI NIPPON PRINTING CO., LTD., Tokyo (JP); YAMAMOTO CHEMICALS, INC., Yao-shi (JP)

( * ) Notice: Subject to any disclaimer, the term of this patent is extended or adjusted under 35 U.S.C. 154(b) by 0 days.

(21) Appl. No.: 16/313,589

(22) PCT Filed: Jun. 23, 2017

(86) PCT No.: PCT/JP2017/023257
§ 371 (c)(1),
(2) Date: Dec. 27, 2018

(87) PCT Pub. No.: WO2018/003708
PCT Pub. Date: Jan. 4, 2018

(65) Prior Publication Data
US 2019/0308931 A1 Oct. 10, 2019

(30) Foreign Application Priority Data
Jun. 28, 2016 (JP) .................... 2016-128190

(51) Int. Cl.
| | | |
|---|---|---|
| C07C 211/64 | (2006.01) |
| C09B 11/24 | (2006.01) |
| C07C 211/53 | (2006.01) |
| C09B 11/16 | (2006.01) |
| C09B 69/10 | (2006.01) |
| C09B 11/12 | (2006.01) |
| B01J 31/00 | (2006.01) |
| B01J 31/04 | (2006.01) |
| C09B 69/02 | (2006.01) |

(52) U.S. Cl.
CPC ............ *C07C 211/64* (2013.01); *B01J 31/00* (2013.01); *B01J 31/04* (2013.01); *C07C 211/53* (2013.01); *C09B 11/12* (2013.01); *C09B 11/16* (2013.01); *C09B 11/24* (2013.01); *C09B 69/02* (2013.01); *C09B 69/103* (2013.01); *C09B 69/109* (2013.01)

(58) Field of Classification Search
CPC .................................................. C07C 211/64
USPC ......................................................... 549/227
See application file for complete search history.

(56) References Cited

U.S. PATENT DOCUMENTS

| | | |
|---|---|---|
| 3,278,436 A | 10/1966 | Dazzi et al. |
| 4,433,145 A | 2/1984 | Wiezer et al. |
| 5,047,531 A | 9/1991 | Cantatore et al. |
| 5,736,557 A | 4/1998 | Hofheinz et al. |
| 5,912,386 A | 6/1999 | Kalz et al. |
| 2014/0039201 A1 | 2/2014 | Okada et al. |
| 2015/0077685 A1 | 3/2015 | Okada et al. |
| 2015/0353472 A1 | 12/2015 | Okada et al. |

(Continued)

FOREIGN PATENT DOCUMENTS

| | | |
|---|---|---|
| DE | 1088020 B | 9/1960 |
| DE | 2613425 A1 | 10/1977 |

(Continued)

OTHER PUBLICATIONS

Nawel Cheikh et al. "A Serendipitous Conversion of Enaminolactone Nitriles With Primary Amines: A New Synthesis of Substituted 2-Aminopyridine Derivatives". Tetrahedron, 2013, vol. 69, No. 3, pp. 1234-1247.

(Continued)

*Primary Examiner* — Taofiq A Solola
(74) *Attorney, Agent, or Firm* — Oliff PLC

(57) ABSTRACT

A compound represented by the following general formula (I):

General Formula (I)

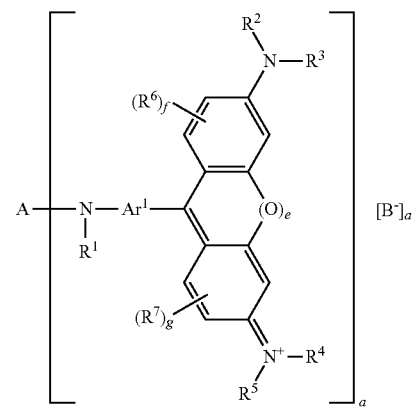

(the symbols in the general formula (I) are as described in the Description),
wherein the compound contains one or more structures selected from the following (i) and (ii):
(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain (Continued)

(ii) at least one of $R^2$, $R^3$, $R^4$ and $R^5$ is a cycloalkyl group optionally containing a substituent group or an aryl group optionally containing a substituent group.

10 Claims, 1 Drawing Sheet

(56) References Cited

U.S. PATENT DOCUMENTS

| 2016/0291489 | A1 | 10/2016 | Sekido et al. |
| 2016/0376443 | A1 | 12/2016 | Ogura et al. |

FOREIGN PATENT DOCUMENTS

| JP | S56-075488 | A | 6/1981 |
| JP | H02-88571 | A | 3/1990 |
| JP | H07-90212 | A | 4/1995 |
| JP | H10-501540 | A | 2/1998 |
| JP | H10-218845 | A | 8/1998 |
| JP | 2013-057052 | A | 3/2013 |
| JP | 2013-57054 | A | 3/2013 |
| JP | 2013-242522 | A | 12/2013 |
| JP | 2015-107471 | A | 6/2015 |
| JP | 2016-88894 | A | 5/2016 |
| JP | 2016-191916 | A | 11/2016 |
| JP | 2016-199618 | A | 12/2016 |
| JP | 2017-165808 | A | 9/2017 |
| WO | 98/057956 | A1 | 12/1998 |

OTHER PUBLICATIONS

R. F. Walker et al. "Spectrophotometric Determination of Aliphatic Isocyanates in the Occupational Atmosphere Part 1. Determination of Total Isocyanate Concentration". Analyst, 1979, vol. 104, No. 1243, pp. 928-936.

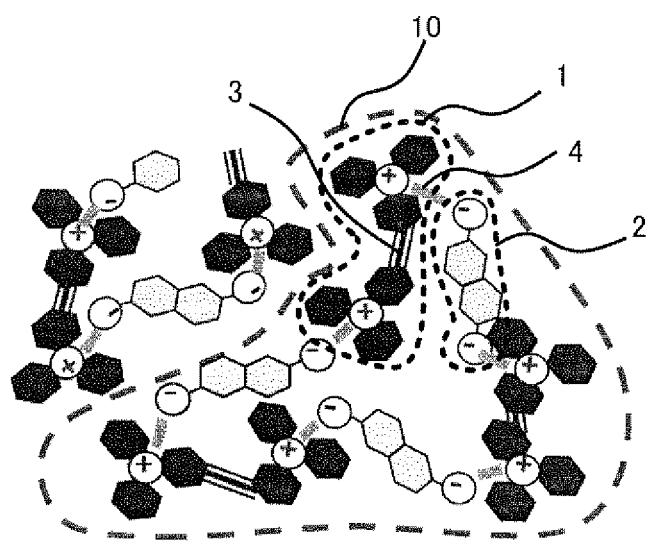

COMPOUND AND INTERMEDIATE THEREOF

TECHNICAL FIELD

The present disclosure relates to a compound with excellent heat resistance and an intermediate for production of the compound.

BACKGROUND ART

Many dyes are conventionally known and broadly classified into natural dyes and synthetic dyes. As the synthetic dyes, examples include, but are not limited to, aniline blue, fuchsine and methyl orange. Most of the synthetic dyes contain an aromatic or heterocyclic ring, and they are each an ionic compound (e.g., a water-soluble dye) or a nonionic compound (e.g., a disperse dye). Ionic dyes are classified into anionic dyes and cationic dyes.

A basic triarylmethane-based dye is a cationic dye and characterized by its color that is relatively deep and clear. Xanthene-based dyes such as rhodamine are characterized by strong fluorescence. Triarylmethane-based dyes and xanthene-based dyes are used in a wide variety of applications such as optical materials, since they have high transmittance.

However, depending on applications, dyes are insufficient in heat resistance or light resistance, and many studies have been made to increase their toughness.

As a color material with excellent heat resistance, the inventors of the present disclosure disclosed a specific color material containing two or more dye skeletons (e.g., Patent Literature 1).

CITATION LIST

Patent Literature 1: Japanese Patent Application Laid-Open (JP-A) No. 2013-057054
Patent Literature 2: JP-A No. 2013-057052
Patent Literature 3: JP-A No. 2013-242522

SUMMARY OF INVENTION

Technical Problem

An object of the disclosed embodiments is to provide a color material with excellent heat resistance.

Solution to Problem

In a first embodiment of the present disclosure, there is provided a compound represented by the following general formula (I):

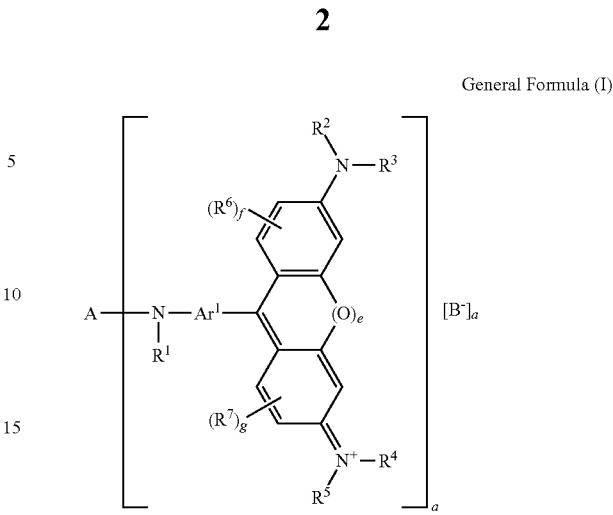

General Formula (I)

where "A" is an "a"-valent organic group in which a carbon atom directly bound to "N" contains no π bond, and the organic group is an aliphatic hydrocarbon group containing a saturated aliphatic hydrocarbon group at least at a terminal position directly bound to "N" and optionally containing O, S, N in a carbon chain, or an aromatic group containing an aliphatic hydrocarbon group at a terminal position directly bound to "N" and optionally containing O, S, N in a carbon chain; each of $R^1$, $R^2$, $R^3$, $R^4$ and $R^5$ is independently a hydrogen atom, an alkyl group optionally containing a substituent group, or an aryl group optionally containing a substituent group; each of $R^6$ and $R^7$ is independently an alkyl group optionally containing a substituent group or an alkoxy group optionally containing a substituent group; $Ar^1$ is a divalent aromatic group optionally containing a substituent group; $B^-$ is a monovalent anion; "a" is an integer of 2 or more; "e" is 0 or 1; each of "f" and "g" is an integer of from 0 to 4; each of "f+e" and "g+e" is from 0 to 4; R's may be the same or different; $R^2$ s may be the same or different; $R^3$s may be the same or different; $R^4$s may be the same or different; $R^5$s may be the same or different; $R^6$s may be the same or different; $R^7$s may be the same or different; $Ar^1$s may be the same or different; "e"s may be the same or different; "f"s may be the same or different; and "g"s may be the same or different, wherein the compound contains one or more structures selected from the following (i) and (ii):

(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain (ii) at least one of $R^2$, $R^3$, $R^4$ and $R^5$ is a cycloalkyl group optionally containing a substituent group or an aryl group optionally containing a substituent group.

In a second embodiment of the present disclosure, there is provided a compound represented by the following general formula (II):

General Formula (II)

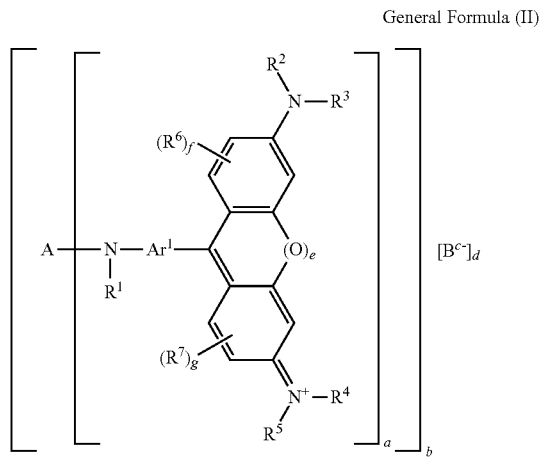

where "A" is an "a"-valent organic group in which a carbon atom directly bound to "N" contains no π bond, and the organic group is an aliphatic hydrocarbon group containing a saturated aliphatic hydrocarbon group at least at a terminal position directly bound to "N" and optionally containing O, S, N in a carbon chain, or an aromatic group containing an aliphatic hydrocarbon group at a terminal position directly bound to "N" and optionally containing O, S, N in a carbon chain; each of $R^1$, $R^2$, $R^3$, $R^4$ and $R^5$ is independently a hydrogen atom, an alkyl group optionally containing a substituent group, or an aryl group optionally containing a substituent group; each of $R^6$ and $R^7$ is independently an alkyl group optionally containing a substituent group or an alkoxy group optionally containing a substituent group; $Ar^1$ is a divalent aromatic group optionally containing a substituent group; $B^{c-}$ is a "c"-valent anion; each of "a" and "c" is an integer of 2 or more; each of "b" and "d" is an integer of 1 or more; "e" is 0 or 1; each of "f" and "g" is an integer of from 0 to 4; each of "f+e" and "g+e" is from 0 to 4; R's may be the same or different; $R^2$s may be the same or different; $R^3$s may be the same or different; $R^4$s may be the same or different; $R^5$s may be the same or different; $R^6$s may be the same or different; $R^7$s may be the same or different; $Ar^1$s may be the same or different; "e"s may be the same or different; "f"s may be the same or different; and "g"s may be the same or different, wherein the compound contains one or more structures selected from the above-mentioned (i) and (ii).

In another embodiment of the present disclosure, there is provided the compound wherein at least one of $R^2$, $R^3$, $R^4$ and $R^5$ is a substituent group represented by the following formula (III) or (IV):

General Formula (III)

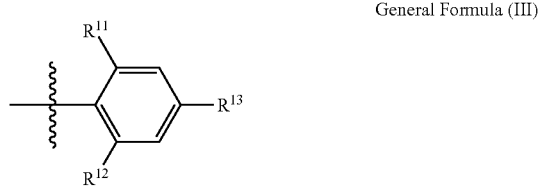

where each of $R^{11}$, $R^{12}$ and $R^{13}$ is independently a hydrogen atom, an alkyl group containing 1 to 4 carbon atoms and optionally containing a substituent group, or an alkoxy group containing 1 to 4 carbon atoms and optionally containing a substituent group, General Formula (IV)

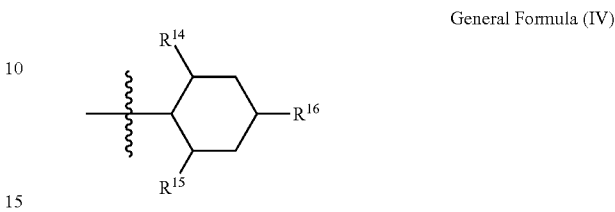

where each of $R^{14}$, $R^{15}$ and $R^{16}$ is independently a hydrogen atom, an alkyl group containing 1 to 4 carbon atoms and optionally containing a substituent group, or an alkoxy group containing 1 to 4 carbon atoms and optionally containing a substituent group.

In another embodiment of the present disclosure, there is provided the compound wherein "A" is a substituent group represented by the following general formula (V):

General Formula (V)

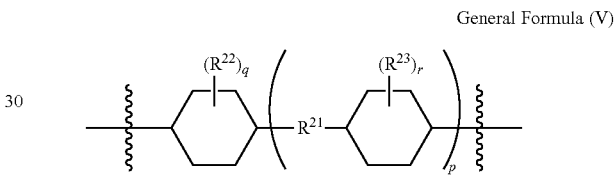

where $R^{21}$ is an alkylene group containing 1 to 3 carbon atoms and optionally containing, as a substituent group, an alkyl group containing 1 to 4 carbon atoms or an alkoxy group containing 1 to 4 carbon atoms; each of $R^{22}$ and $R^{23}$ is independently an alkyl group containing 1 to 4 carbon atoms or an alkoxy group containing 1 to 4 carbon atoms; "p" is an integer of from 1 to 3; each of "q" and "r" is independently an integer of from 0 to 4; when $R^{21}$s are present, they may be the same or different; when two or more $R^{22}$s are present, they may be the same or different; when two or more $R^{23}$s are present, they may be the same or different; and when two or more "r"s are present, they may be the same or different.

In another embodiment of the present disclosure, there is provided the compound wherein the anion represented by $B^{c-}$ is a heteropolyoxometalate containing one or more elements selected from tungsten and molybdenum.

In another embodiment of the present disclosure, there is provided an intermediate for production of the compound of the disclosed embodiments, wherein the intermediate is represented by the following general formula (VI):

General Formula (VI)

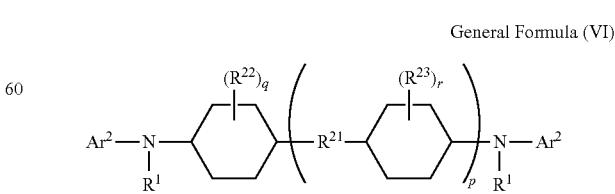

where $R^1$ is a hydrogen atom, an alkyl group optionally containing a substituent group, or an aryl group optionally containing a substituent group; Ar² is a monovalent aromatic group optionally containing a substituent group; R²¹ is an alkylene group containing 1 to 3 carbon atoms and optionally containing, as a substituent group, an alkyl group containing 1 to 4 carbon atoms or an alkoxy group containing 1 to 4 carbon atoms; each of R²² and R²³ is independently an alkyl group containing 1 to 4 carbon atoms or an alkoxy group containing 1 to 4 carbon atoms; "p" is an integer of from 1 to 3; each of "q" and "r" is independently an integer of from 0 to 4; R's may be the same or different; Ar²s may be the same or different; when two or more R²¹s are present, they may be the same or different; when two or more R²²s are present, they may be the same or different; when two or more R²³s are present, they may be the same or different; and when two or more "r"s are present, they may be the same or different two or more.

Advantageous Effects of Invention

According to the disclosed embodiments, a compound with excellent heat resistance can be provided.

BRIEF DESCRIPTION OF DRAWING

FIG. 1 is a schematic view of the molecular association state of a compound according to a second embodiment.

DESCRIPTION OF EMBODIMENTS

Hereinafter, the embodiments of the present disclosure and examples thereof will be described.

In the present disclosure, light encompasses electromagnetic waves with wavelengths in the visible and non-visible range, and radial rays. Radial rays include microwaves and electron beams, more specifically, electromagnetic waves with wavelengths of 5 µm or less, and electron beams.

[Compounds]

The compound of the first embodiment of the present disclosure (hereinafter, it may be simply referred to as "first compound") is a compound represented by the following general formula (I):

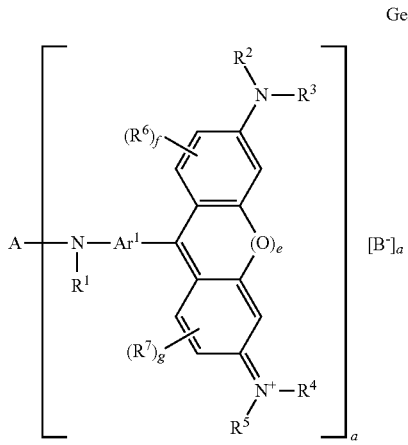

General Formula (I)

where "A" is an "a"-valent organic group in which a carbon atom directly bound to "N" contains no π bond, and the organic group is an aliphatic hydrocarbon group containing a saturated aliphatic hydrocarbon group at least at a terminal position directly bound to "N" and optionally containing O, S, N in a carbon chain, or an aromatic group containing an aliphatic hydrocarbon group at a terminal position directly bound to "N" and optionally containing O, S, N in a carbon chain; each of R¹, R², R³, R⁴ and R⁵ is independently a hydrogen atom, an alkyl group optionally containing a substituent group, or an aryl group optionally containing a substituent group; each of R⁶ and R⁷ is independently an alkyl group optionally containing a substituent group or an alkoxy group optionally containing a substituent group; Ar¹ is a divalent aromatic group optionally containing a substituent group; B⁻ is a monovalent anion; "a" is an integer of 2 or more; "e" is 0 or 1; each of "f" and "g" is an integer of from 0 to 4; each of "f+e" and "g+e" is from 0 to 4; R's may be the same or different; R² s may be the same or different; R³s may be the same or different; R⁴s may be the same or different; R⁵s may be the same or different; R⁶s may be the same or different; R⁷s may be the same or different; Ar¹s may be the same or different; "e"s may be the same or different; "f"s may be the same or different; and "g"s may be the same or different, wherein the compound contains one or more structures selected from the following (i) and (ii):

(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain (ii) at least one of R², R³, R⁴ and R⁵ is a cycloalkyl group optionally containing a substituent group or an aryl group optionally containing a substituent group.

The compound of the second embodiment of the present disclosure (hereinafter, it may be simply referred to as "second compound") is a compound represented by the following general formula (II):

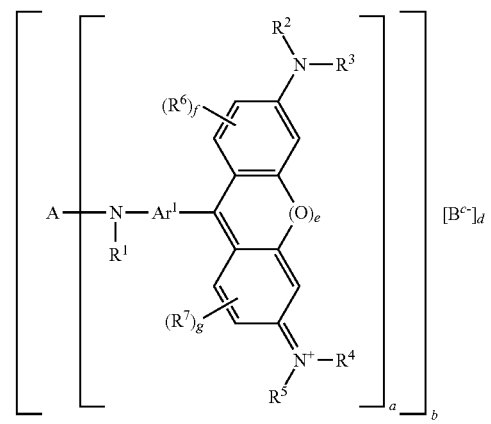

General Formula (II)

where "A" is an "a"-valent organic group in which a carbon atom directly bound to "N" contains no π bond, and the organic group is an aliphatic hydrocarbon group containing a saturated aliphatic hydrocarbon group at least at a terminal position directly bound to "N" and optionally containing O, S, N in a carbon chain, or an aromatic group containing an aliphatic hydrocarbon group at a terminal position directly bound to "N" and optionally containing O, S, N in a carbon chain; each of R¹, R², R³, R⁴ and R⁵ is independently a hydrogen atom, an alkyl group optionally containing a substituent group, or an aryl group optionally containing a substituent group; each of R⁶ and R⁷ is independently an alkyl group optionally containing a substituent group or an alkoxy group optionally containing a substituent group; $Ar^1$ is a divalent aromatic group optionally containing a substituent group; $B^{c-}$ is a "c"-valent anion; each of "a" and "c" is an integer of 2 or more; each of "b" and "d" is an integer of 1 or more; "e" is 0 or 1; each of "f" and "g" is an integer of from 0 to 4; each of "f+e" and "g+e" is from 0 to 4; R's may be the same or different; $R^2$s may be the same or different; $R^3$s may be the same or different; $R^4$s may be the same or different; $R^5$s may be the same or different; $R^6$s may be the same or different; $R^7$s may be the same or different; $Ar^1$s may be the same or different; "e"s may be the same or different; "f"s may be the same or different; and "g"s may be the same or different, wherein the compound contains one or more structures selected from the above-mentioned (i) and (ii).

A point in common between the first and second compounds, is that a color-forming cation is represented by the following general formula (A) and the compounds contain one or more structures selected from the following (i) and (ii):

(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain (ii) at least one of $R^2$, $R^3$, $R^4$ and $R^5$ is a cycloalkyl group optionally containing a substituent group or an aryl group optionally containing a substituent group.

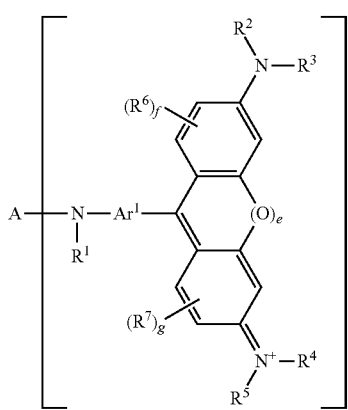

General Formula (A)

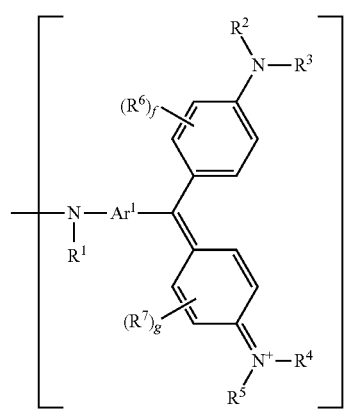

General Formula (B)

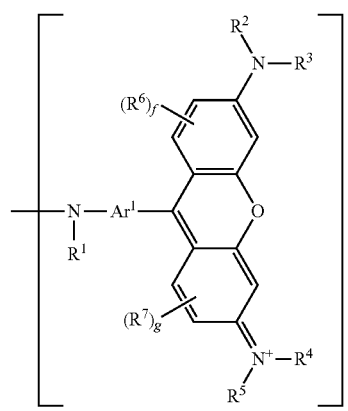

General Formula (C)

(The symbols in the general formulae (B) and (C) are the same as those in the general formula (A).)

Also, the first and second compounds of the present disclosure have excellent heat resistance, since they contain one or more structures selected from the above-mentioned (i) and (ii).

In the present disclosure, "excellent heat resistance" means that the compound shows a small color change before and after heating.

The inventors of the present disclosure made a detailed study from the viewpoint of suppressing a change in the color of the compound before and after heating. As a result, they found that excellent heat resistance is obtained when the general formula (A) satisfies at least one of the following (i) and (ii):

(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain (ii) at least one of $R^2$, $R^3$, $R^4$ and $R^5$ is a cycloalkyl group optionally containing a substituent group or an aryl group optionally containing a substituent group.

The reason why excellent heat resistance is obtained when the compound contains at least one of the above-specified structures, is not absolutely clear. However, it is estimated as follows.

In the general formula (A), "A" is a linking group linking two or more color-forming moieties. It was estimated that the heat resistance of the compound is increased when the linking group "A" contains a tough cyclic skeleton. However, it is estimated that the color-forming moieties linked by (The symbols in the general formula (A) are the same as those in the general formulae (I) and (II).)

The general formula (A) contains one or more structures selected from a triarylmethane moiety represented by the following general formula (B) (in the case where "e" is 0) and a xanthene moiety represented by the following general formula (C) (in the case where "e" is 1). Since the triarylmethane and xanthene moieties have excellent coloring properties, the first and second compounds of the present disclosure can be suitably used as color materials.

For the linking group "A" linking the triarylmethane and xanthene moieties, the carbon atom directly bound to "N" contains no n bond. Therefore, two or more triarylmethane and xanthene moieties present per molecule of the compound, become independent color-forming moieties.

the cyclic skeleton are more rigid than the case of being linked by a chain skeleton, resulting in a decrease in the freedom of rotational motion. It was estimated that since the triarylmethane or xanthene moiety, which is a color moiety, contains a bulky structure, if its rotational motion is suppressed, free molecular motion is inhibited at the time of heating, which causes distortion and, as a result, becomes a cause for molecular decomposition. In the compound of the present disclosure, when "A" is the above-specified aliphatic hydrocarbon group containing two or more alicyclic hydrocarbon groups, rotational motion is ensured at the linking moiety linking at least two or more alicyclic hydrocarbon groups. Therefore, the two or more color-forming moieties are allowed to move independently to some degree. Therefore, distortion is less likely to occur and, as a result, the heat resistance of the compound is increased.

$R^2$ to $R^5$ are substituent groups bound to nitrogen atoms constituting the color-forming moieties. Since at least one of $R^2$ to $R^5$ is the specific aryl or cycloalkyl group, due to steric hindrance, the color-forming moieties are less susceptible to intermolecular interaction. Therefore, it is estimated that the color-forming moieties are less susceptible to influences of heat, thus obtaining increased heat resistance. When at least one of $R^2$ to $R^5$ is the specific aryl or cycloalkyl group, due to the effect of the substituent group, the aryl or cycloalkyl group obtains a structure that is twisted toward a side perpendicular to a conjugated plane formed by the color-forming moieties to which the aryl or cycloalkyl group is bound. As a result, it is estimated that electrons are localized in the color-forming moieties, and the reactivity of conjugated cation increases to increase the strength of an ionic bond with counter anion, thereby stabilizing ion pairs and increasing the heat resistance of the compound.

Due to the above reason, the heat resistance of the compound is increased by obtaining at least one of the above-mentioned structures (i) and (ii).

Hereinafter, the structures of the first and second compounds of the present disclosure will be described. More specifically, the cation represented by the general formula (A), which is common to the first and second compounds of the present disclosure, will be described first. Next, the anion of the first compound and that of the second compound will be described.

<Cations Represented by the General Formula (A)>

In the general formula (A), the linking group "A" is an "a"-valent organic group in which a carbon atom directly bound to "N" (nitrogen atom) contains no n bond, and the organic group is an aliphatic hydrocarbon group containing a saturated aliphatic hydrocarbon group at least at a terminal position directly bound to "N" and optionally containing O (oxygen atom), S (sulfur atom), N in a carbon chain, or an aromatic group containing an aliphatic hydrocarbon group at a terminal position directly bound to "N" and optionally containing O, S, N in a carbon chain. Since the carbon atom directly bound to "N" contains no n bond, the color characteristics of the color-forming moiety, such as color tone and transmittance, are not affected by the linking group "A" and other color-forming moieties.

In "A", as long as the carbon atom being at the terminal position and directly bound to "N" contains no n bond, the aliphatic hydrocarbon group containing a saturated aliphatic hydrocarbon group at least at a terminal position directly bound to "N", may be straight-chain, branched-chain or cyclic, may contain an unsaturated bond in carbon atoms except the one in the terminal position, may contain a substituent group, or may contain O, S, N in the carbon chain. For example, a carbonyl group, a carboxyl group, an oxycarbonyl group and/or an amide group may be contained, and the hydrogen atom of the hydrocarbon group may be substituted by a halogen atom, etc.

Also in "A", as the aromatic group containing an aliphatic hydrocarbon group, examples include, but are not limited to, a monocyclic or polycyclic aromatic group which contains an aliphatic hydrocarbon group containing a saturated aliphatic hydrocarbon group at least at the terminal position directly bound to "N". The aromatic group may contain a substituent group, and it may be a heterocyclic ring containing O, S, N.

Particularly, from the viewpoint of skeleton toughness, it is preferable that "A" contains an alicyclic hydrocarbon group or an aromatic group.

As the alicyclic hydrocarbon group, examples include, but are not limited to, groups containing cyclohexane, cyclopentane, norbornane, bicyclo[2.2.2]octane, tricyclo[5.2.1.0$^{2.6}$]decane and adamantane. As the aromatic group, examples include, but are not limited to, a group containing a benzene ring and a group containing a naphthalene ring.

In the present disclosure, from the viewpoint of obtaining both the toughness and the molecular motion freedom and increasing the heat resistance of the compound, it is preferable that "A" satisfies the above-mentioned (i), that is, "A" is an aliphatic hydrocarbon group containing two or more alicyclic hydrocarbon groups, containing a saturated aliphatic hydrocarbon group at a terminal position directly bound to "N", and optionally containing O, S, N in a carbon chain. It is also preferable that "A" is an aliphatic hydrocarbon group containing two or more cycloalkylene groups, containing a saturated aliphatic hydrocarbon group at a terminal position directly bound to "N", and optionally containing O, S, N in a carbon chain. It is more preferable that "A" contains such a structure that two or more alicyclic hydrocarbon groups are bound by a straight-chain or branched-chain aliphatic hydrocarbon group.

The two or more alicyclic hydrocarbon groups may be the same as or different from each other. As the alicyclic hydrocarbon groups, examples include, but are not limited to, the above-mentioned alicyclic hydrocarbon groups. Of them, cyclohexane and cyclopentane are preferred.

In the present disclosure, from the viewpoint of the heat resistance, it is preferable that "A" is a substituent group represented by the following general formula (V):

General Formula (V)

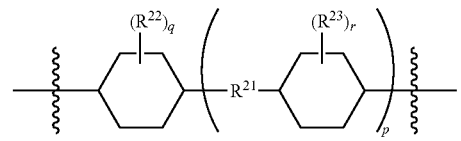

where $R^{21}$ is an alkylene group containing 1 to 3 carbon atoms and optionally containing, as a substituent group, an alkyl group containing 1 to 4 carbon atoms or an alkoxy group containing 1 to 4 carbon atoms; each of $R^{22}$ and $R^{23}$ is independently an alkyl group containing 1 to 4 carbon atoms or an alkoxy group containing 1 to 4 carbon atoms; "p" is an integer of from 1 to 3; each of "q" and "r" is independently an integer of from 0 to 4; when two or more $R^{21}$s are present, they may be the same or different; when two or more $R^{22}$s are present, they may be the same or different; when two or more $R^{23}$s are present, they may be the same or different; and when two or more "r"s are present, they may be the same or different.

From the viewpoint of obtaining both the toughness and the thermal motion of the color-forming moieties and increasing the heat resistance, $R^{21}$ is preferably an alkylene group containing 1 to 3 carbon atoms. As the alkylene group, examples include, but are not limited to, a methylene group, an ethylene group and a propylene group. Of them, a methylene group and an ethylene group are preferred, and a methylene group is more preferred.

As the alkyl group containing 1 to 4 carbon atoms, examples include, but are not limited to, a methyl group, an ethyl group, a propyl group and a butyl group. They may be straight-chain or branched-chain.

As the alkoxy group containing 1 to 4 carbon atoms, examples include, but are not limited to, a methoxy group, an ethoxy group, a propoxy group and a butoxy group. They may be straight-chain or branched-chain.

Examples of the alkyl group containing 1 to 4 carbon atoms and the alkoxy group containing 1 to 4 carbon atoms as $R^{22}$ and $R^{23}$ include, but are not limited to, the above-mentioned substituent groups that $R^{21}$ may contain.

From the viewpoint of the heat resistance, it is preferable that the number of cyclohexanes (cyclohexylene groups) in the general formula (V) is from 2 to 4, that is, "p" is from 1 to 3. It is more preferable that p is 1 or 2.

The numbers of the substituent groups $R^{22}$ and $R^{23}$ that the cyclohexylene group may contain, are not particularly limited. From the viewpoint of the heat resistance, each of the numbers is preferably from 1 to 3, and more preferably 1 or 2. That is, it is preferable that each of "q" and "r" is an integer of from 1 to 3, and it is more preferable that each of "q" and "r" is an integer of 1 or 2.

As the linking group "A", preferred examples include, but are not limited to, the following groups.

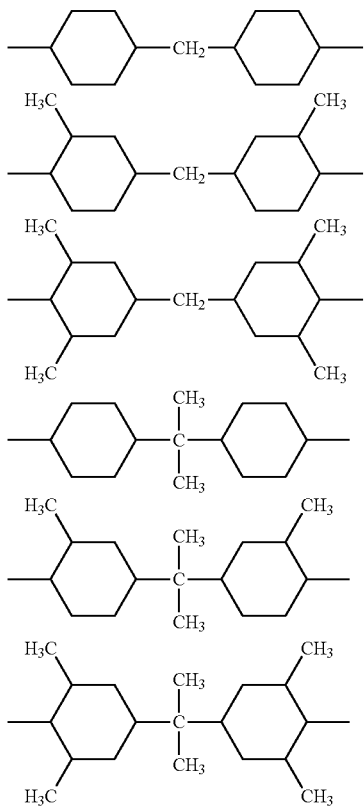

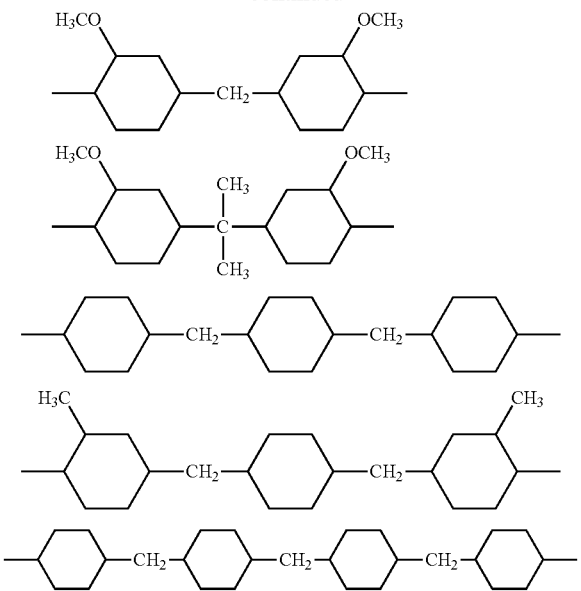

Each of $R^1$ to $R^5$ is independently a hydrogen atom, an alkyl group optionally containing a substituent group, or an aryl group optionally containing a substituent group.

The alkyl group as $R^1$ is not particularly limited. As the alkyl group, examples include, but are not limited to, a straight-chain, branched-chain or cyclic alkyl group containing 1 to 20 carbon atoms. The alkyl group as $R^1$ is preferably a straight-chain or branched-chain alkyl group containing 1 to 8 carbon atoms, more preferably a straight-chain or branched-chain alkyl group containing 1 to 5 carbon atoms, and still more preferably an ethyl group or a methyl group. As the substituent group that the alkyl group as $R^1$ may contain, examples include, but are not limited to, an aryl group, a halogen atom and a hydroxyl group. As the substituted alkyl group, examples include, but are not limited to, a benzyl group. The aryl group as $R^1$ is not particularly limited. As the aryl group, examples include, but are not limited to, a phenyl group and a naphthyl group. As the substituent group that the aryl group as $R^1$ may contain, examples include, but are not limited to, an alkyl group, an alkoxy group, a halogen atom and a hydroxyl group.

As the alkyl group optionally containing a substituent group or the aryl group optionally containing a substituent group as $R^2$, $R^3$, $R^4$ and $R^5$, the examples provided above as $R^1$ can be preferably used. From the viewpoint of the heat resistance, it is preferable that at least one of $R^2$ to $R^5$ is a cycloalkyl group optionally containing a substituent group or an aryl group optionally containing a substituent group. Since at least one of $R^2$ to $R^5$ contains a cycloalkyl group or an aryl group, intermolecular interaction is reduced by steric hindrance and, as a result, influences of heat on the color-forming moieties can be reduced. Therefore, the heat resistance of the compound is excellent.

When at least one of $R^2$ to $R^5$ is an aryl group or a cycloalkyl group, compared to the case of not containing at least one of the structures (i) and (ii), the reactivity of conjugated cation increases to increase the strength of an ionic bond with counter anion, thereby stabilizing ion pairs. Therefore, the compound obtains excellent heat resistance.

For the compound of the disclosed embodiments, from the viewpoint of the heat resistance, it is preferable that at least one of $R^2$ to $R^5$ is a substituent group represented by the following formula (III) or (IV):

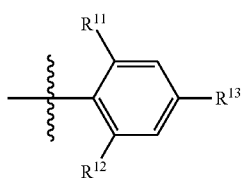

General Formula (III)

where each of $R^{11}$, $R^{12}$ and $R^{13}$ is independently a hydrogen atom, an alkyl group containing 1 to 4 carbon atoms and optionally containing a substituent group, or an alkoxy group containing 1 to 4 carbon atoms and optionally containing a substituent group,

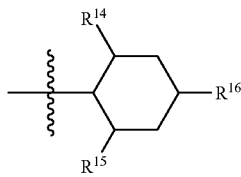

General Formula (IV)

where each of $R^{14}$, $R^{15}$ and $R^{16}$ is independently a hydrogen atom, an alkyl group containing 1 to 4 carbon atoms and optionally containing a substituent group, or an alkoxy group containing 1 to 4 carbon atoms and optionally containing a substituent group.

Examples of the alkyl group containing 1 to 4 carbon atoms as $R^{11}$, $R^{12}$, $R^{13}$, $R^{14}$, $R^{15}$ and $R^{16}$ include a methyl group, an ethyl group, a propyl group and a butyl group. The alkyl group may be straight-chain or branched-chain. As the alkoxy group containing 1 to 4 carbon atoms, examples include a methoxy group, an ethoxy group, a propoxy group and a butoxy group. The alkoxy group may be straight-chain or branched-chain.

As the substituent group that the alkyl group and the alkoxy group may contain, examples include, but are not limited to, a halogen atom and a hydroxyl group.

In the case of containing a substituent group represented by the general formula (III), from the viewpoint of the heat resistance, it is preferable that at least one of $R^{11}$, $R^{12}$ and $R^{13}$ is an alkyl group containing 1 to 4 carbon atoms and optionally containing a substituent group, or an alkoxy group containing 1 to 4 carbon atoms and optionally containing a substituent group. It is more preferable that at least one of $R^{11}$ and $R^{12}$ is an alkyl group containing 1 to 4 carbon atoms and optionally containing a substituent group, or an alkoxy group containing 1 to 4 carbon atoms and optionally containing a substituent group.

In the case of containing a substituent group represented by the general formula (IV), from the viewpoint of the heat resistance, it is preferable that at least one of $R^{14}$, $R^{15}$ and $R^{16}$ is an alkyl group containing 1 to 4 carbon atoms and optionally containing a substituent group, or an alkoxy group containing 1 to 4 carbon atoms and optionally containing a substituent group. It is more preferable that at least one of $R^{14}$ and $R^{15}$ is an alkyl group containing 1 to 4 carbon atoms and optionally containing a substituent group, or an alkoxy group containing 1 to 4 carbon atoms and optionally containing a substituent group.

As the substituent group represented by the general formula (III) and the substituent group represented by the general formula (IV), preferred examples include, but are not limited to, the following groups.

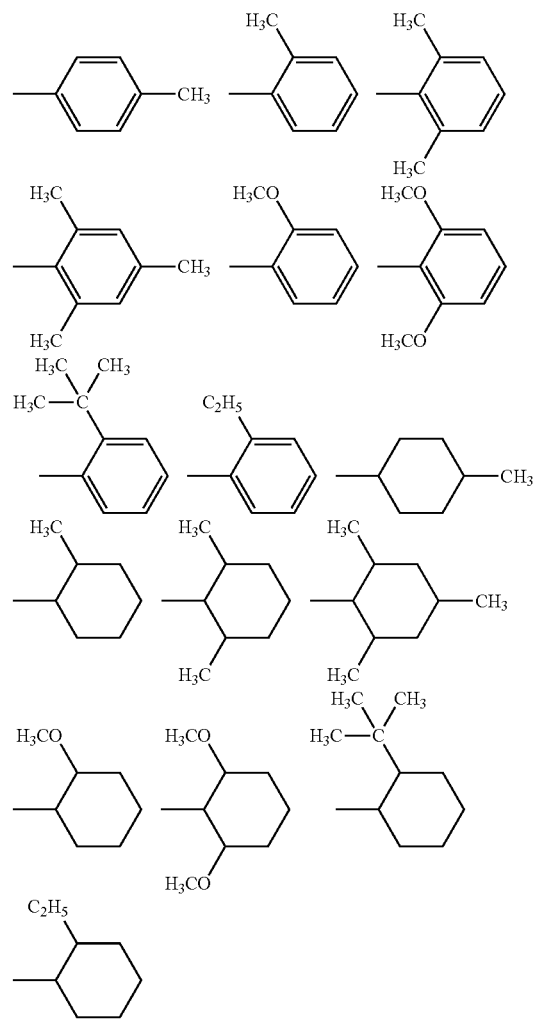

Each of $R^6$ and $R^7$ is independently an alkyl group optionally containing a substituent group or an alkoxy group optionally containing a substituent group. The alkyl group as $R^6$ and $R^7$ is not particularly limited. It is preferably a straight-chain or branched-chain alkyl group containing 1 to 8 carbon atoms, and more preferably an alkyl group containing 1 to 4 carbon atoms. As the alkyl group containing 1 to 4 carbon atoms, examples include a methyl group, an ethyl group, a propyl group and a butyl group, and the alkyl group may be straight-chain or branched-chain.

The alkoxy group as $R^6$ and $R^7$ is not particularly limited. It is preferably a straight-chain or branched-chain alkoxy group containing 1 to 8 carbon atoms, and more preferably an alkoxy group containing 1 to 4 carbon atoms. As the alkoxy group containing 1 to 4 carbon atoms, examples include a methoxy group, an ethoxy group, a propoxy group and a butoxy group, and the alkoxy group may be straight-chain or branched-chain.

Each of the number of the substituent groups of $R^6$ and the number of the substituent groups of $R^7$, that is, each of "f"

and "g" is independently an integer of from 0 to 4. Each of them is preferably an integer of from 0 to 2, and more preferably an integer of 0 or 1.

Each of $R^6$ and $R^7$ may be substituted at any position of an aromatic ring with a resonance structure in the triarylmethane or xanthene skeleton. It is preferable that each of $R^6$ and $R^7$ is substituted at the meta-position, relative to the substitution position of the amino group represented by —$NR^2R^3$ or —$NR^4R^5$.

The divalent aromatic group as $Ar^1$ is not particularly limited. The aromatic group may be an aromatic hydrocarbon group comprising a carbon ring, or a heterocyclic group. As the aromatic hydrocarbon in the aromatic hydrocarbon group, examples include, but are not limited to, a benzene ring; condensed polycyclic aromatic hydrocarbons such as a naphthalene ring, a tetralin ring, an indene ring, a fluorene ring, an anthracene ring and a phenanthrene ring; and chain polycyclic hydrocarbons such as biphenyl, terphenyl, diphenylmethane, triphenylmethane and stilbene. The chain polycyclic hydrocarbons may contain O, S, N in the chain skeleton, such as diphenyl ether. Meanwhile, as the heterocyclic ring in the heterocyclic group, examples include, but are not limited to, 5-membered heterocyclic rings such as furan, thiophene, pyrrole, oxazole, thiazole, imidazole and pyrazole; 6-membered heterocyclic rings such as pyran, pyrone, pyridine, pyrone, pyridazine, pyrimidine and pyrazine; and condensed polycyclic heterocyclic rings such as benzofuran, thionaphthene, indole, carbazole, coumarin, benzo-pyrone, quinoline, isoquinoline, acridine, phthalazine, quinazoline and quinoxaline. These aromatic groups may further contain, as a substituent group, an alkyl group, an alkoxy group, a hydroxyl group, a halogen atom, etc.

In the general formula (A), "a" is the number of the color-forming moieties constituting the cation, and "a" is an integer of 2 or more. The upper limit of "a" is not particularly limited. From the viewpoint of ease of production, "a" is preferably 4 or less, and more preferably 3 or less.

For the cation represented by the general formula (A), the molecular weight is preferably 1000 or more, more preferably 1200 or more, and still more preferably 1300 or more, from the point of view that the compound obtains excellent heat resistance and a color change of the compound is easily suppressed at the time of heating.

<Monovalent Anion>

The first compound of the present disclosure contains a monovalent anion (B). For the first compound containing the monovalent anion, dissociation of anion and cation is likely to occur in an alcohol-based or ketone-based solvent; the solubility of the first compound into the solvent increases; and the first compound is likely to adsorb to various kinds of substrates. Therefore, the first compound obtains excellent dyeing properties. Once the first compound is fixed onto a substrate, the first compound is less likely to discolor and is excellent in fixability, even when exposed to high temperature and high humidity.

The monovalent anion is not particularly limited and may be an organic or inorganic anion. As used herein, the organic anion means an anion containing at least one carbon atom. The inorganic anion means an anion not containing a carbon atom. As the inorganic anion, examples include, but are not limited to, a nitrate ion ($NO^-$), a perchlorate ion ($ClO_4^-$), and halide ions such as a fluoride ion, a chloride ion, a bromide ion and an iodide ion.

When $B^-$ is an organic anion, the structure is not particularly limited. $B^-$ is preferably an organic group containing an anionic substituent group.

As the anionic substituent group, examples include, but are not limited to, imide acid groups such as —$SO_2N^-SO_2CH_3$, —$SO_2N^-COCH_3$, —$SO_2N^-SO_2CF_3$, —$SO_2N^-COCF_3$, —$CF_2SO_2N^-SO_2CH_3$, —$CF_2SO_2N^-COCH_3$, —$CF_2SO_2N^-SO_2CF_3$, and —$CF_2SO_2N^-COCF_3$, and substituent groups such as —$SO_3^-$, —$CF_2SO_3^-$, —$COO^-$ and —$CF_2COO^-$.

Of them, imide acid groups, —$SO_3^-$ and —$CF_2SO_3^-$ are preferred, and —$SO_3^-$ (sulfonato group) is more preferred, from the viewpoint of availability of raw materials, production cost and, due to their high acidity, being highly effective in stabilizing cation to maintain a color thus formed.

The organic group to which the anionic substituent group is introduced by substitution, is not particularly limited. As the organic group, examples include, but are not limited to, a straight-chain, branched-chain or cyclic, saturated or unsaturated hydrocarbon group, a monocyclic or polycyclic aromatic group, and combinations thereof. They may contain a heteroatom such as O, S, N in the carbon chain, or they may contain a carbonyl group, a carboxy group, an oxycarbonyl group or an amide group, and a hydrogen atom may be substituted by a substituent group. As the substituent group that the organic group may contain, examples include, but are not limited to, a halogen atom.

As the organic group to which the anionic substituent group is introduced by substitution, examples include, but are not limited to, hydrocarbons such as cyclopropane, cyclobutane, cyclopentane, cyclohexane, norbornane, bicyclo[2,2,2]hexane, bicyclo[3,2,3]octane and adamantane, and aromatic compounds such as benzene, naphthalene, anthracene, phenanthrene, pyrene, triphenylene, fluorene, furan, thiophene, pyrrole, imidazole, pyran, pyridine, pyrimidine, pyrazine, triazine, indole, purine, quinoline, isoquinoline, xanthene and carbazole. In addition, the organic group may contain a substituent group such as a halogen atom and an alkyl group.

The organic group to which the anionic substituent group is introduced by substitution, is preferably a monocyclic aromatic hydrocarbon group, a polycyclic aromatic hydrocarbon group or a combination thereof, from the viewpoint of ease of introduction of the anionic substituent group.

When it is aimed at preventing the occurrence of a color change due to the anion, an organic group having an absorption maximum in a wavelength range of 400 nm or less, is preferably used. As the organic group having an absorption maximum in a wavelength range of 400 nm or less, examples include, but are not limited to, organic groups comprising condensed polycyclic carbon rings such as naphthalene, tetralin, indene, fluorene, anthracene and phenanthrene; organic groups comprising chain polycyclic hydrocarbons such as biphenyl, terphenyl, diphenylmethane, triphenylmethane and stilbene; organic groups comprising 5-membered heterocyclic rings such as furan, thiophene, pyrrole, oxazole, thiazole, imidazole and pyrazole; aromatic compounds comprising 6-membered heterocyclic rings such as pyran, pyrone, pyridine, pyridazine, pyrimidine and pyrazine; and organic groups comprising condensed polycyclic heterocyclic rings such as benzofuran, thionaphthene, indole, carbazole, coumarin, benzo-pyrone, quinoline, isoquinoline, acridine, phthalazine, quinazoline and quinoxaline.

Also, as the organic group to which the anionic substituent group is introduced by substitution, a skeleton derived from azo dye, anthraquinone dye, triphenylmethane dye, xanthene dye, phthalocyanine dye or indigo dye, each of which is an organic or organometallic compound, may be used. Also, a conventionally-known acid dye, a direct dye or an acidic mordant dye may be used.

When the dye-derived skeleton, the acid dye, the direct dye, the acidic mordant dye or the like is used, the color tone of a color material thus obtained is changed, and the color tone of the first compound can be controlled to a desired color tone.

<Divalent or Higher Anion>

The second compound of the present disclosure contains a divalent or higher anion ($B^{c-}$). As shown by the example in FIG. 1, it is estimated that in the second compound, a molecular association 10 in which plural molecules are continuously connected through ionic bonds and associated, is formed by using a divalent or higher cation 1 in combination with a divalent or higher anion 2. Since the molecular association acts as one molecule in an aggregate of the color material, it is estimated that the apparent molecular weight of the molecular association is much larger than that of a conventional salt-forming compound in which anions and cations bind to each other on a one-on-one basis, and the molecular association contributes to an increase in the heat resistance of the second compound.

The molecular association 10 contains the ionic bonds. Therefore, when a continuous ion association is formed by using a counter anion that "c" is 2 or more, many ionic bonds are contained in the association. Therefore, when "c" is 2 or more, the effect of increasing ionic bond strength which is obtained in the case of containing at least one of the structures (i) and (ii), is higher than the case where "c" is 1, and heat resistance and reliability such as suppression of elution from a coating film, is increased.

The divalent or higher anion ($B^{c-}$) is not particularly limited and may be an organic or inorganic anion.

When $B^{c-}$ is an organic anion, the structure is not particularly limited. The organic anion is preferably an organic group containing an anionic substituent group.

As the anionic substituent group, examples include, but are not limited to, imide acid groups such as $—SO_2N^-SO_2CH_3$, $—SO_2N^-COCH_3$, $—SO_2N^-SO_2CF_3$, $—SO_2N^-COCF_3$, $—CF_2SO_2N^-SO_2CH_3$, $—CF_2SO_2N^-COCH_3$, $—CF_2SO_2N^-SO_2CF_3$, and $—CF_2SO_2N^-COCF_3$, and substituent groups such as $—SO_3^-$, $—CF_2SO_3^-$, $—PO_3^{2-}$, $—COO^-$, $—CF_2PO_3^{2-}$, and $—CF_2COO^-$.

From the viewpoint of stabilizing cation and stabilizing the color formed by the color material, it is preferable to use two or more monovalent anionic substituent groups. From the viewpoint of availability of raw materials, production cost and, due to their high acidity, being highly effective in stabilizing cation to maintain the color thus formed, imide acid groups, $—SO_3^-$ and $—CF_2SO_3^-$ are preferred, and $—SO_3^-$ (sulfonato group) is more preferred.

In the case of introducing two or more anionic substituent groups, they may be the same substituent groups or different substituent groups.

The organic group to which the anionic substituent group is bound by substitution, is not particularly limited. As the organic group, the same organic group as that of the monovalent anion may be used.

On the other hand, when $B^{c-}$ is an inorganic anion, the structure and composition is not particularly limited, as long as it is an inorganic oxoacid or a dehydrated condensate thereof. As the inorganic anion, examples include, but are not limited to, anions of divalent or higher oxoacids (e.g., phosphate ion, sulfate ion, chromate ion, tungstate ion ($WO_4^{2-}$) and molybdate ion ($MoO_4^{2-}$)), polyoxometalate ions formed by condensation of oxoacids, and mixtures thereof.

The polyoxometalate may be isopolyoxometalate ion $(M_mO_n)^{c-}$ or heteropolyoxometalate ion $(X_lM_mO_n)^{c-}$. In the ionic formulae, "M" is a polyatom; "X" is a heteroatom; "m" is the compositional ratio of the polyatom; and "n" is the compositional ratio of the oxygen atom. As the polyatom (M), examples include, but are not limited to, Mo, W, V, Ti and Nb. As the heteroatom (X), examples include, but are not limited to, Si, P, As, S, Fe and Co. A counter cation such as $Na^+$ or $H^+$ may be contained in a part of the polyoxometalate.

From the viewpoint of excellent heat resistance, preferred is a polyoxometalate containing one or more elements selected from tungsten (W) and molybdenum (Mo).

As the polyoxometalate, examples include, but are not limited to, a tungstate ion $[W_{10}O_{32}]^{4-}$ and a molybdate ion $[Mo_6O_{19}]^{2-}$, which are isopolyoxometalates, and phosphotungstate ions $[PW_{12}O_{40}]^{3-}$ and $[P_2W_{18}O_{62}]^{6-}$, a silicotungstate ion $[SiW_{12}O_{40}]^{4-}$, a phosphomolybdate ion $[PMo_{12}O_{40}]^{3-}$, a silicomolybdate ion $[SiMo_{12}O_{40}]^{4-}$, phosphotungstic molybdate ions $[PW_{12-x}Mo_xO_{40}]^{3-}$ (where x is an integer of from 1 to 11) and $[P_2W_{18-y}Mo_yO_{62}]^{6-}$ (where y is an integer of from 1 to 17) and a silicotungstic molybdate ion $[SiW_{12-x}Mo_xO_{40}]^{4-}$ (where x is an integer of from 1 to 11), which are all heteropolyoxometalates. Of them, from the viewpoint of heat resistance and availability of raw materials, the polyoxometalate containing at least one of tungsten (W) and molybdenum (Mo) is preferably a heteropolyoxometalate, and more preferably a heteropolyoxometalate containing phosphorus (P).

The polyoxometalate is still more preferably one selected from the group consisting of phosphotungstic molybdate ions $[PW_{10}Mo_2O_{40}]^{3-}$ and $[PW_{11}Mo_1O_{40}]^{3-}$ and phosphotungstate ion $[PW_{12}O_{40}]^{3-}$, from the viewpoint of the heat resistance.

The content ratio of the tungsten to the molybdenum is not particularly limited. Particularly from the viewpoint of excellent heat resistance, the molar ratio of the tungsten to the molybdenum is preferably from 100:0 to 85:15, and more preferably from 100:0 to 90:10.

As the divalent or higher anion ($B^{c-}$), the above-mentioned polyoxometalate anions can be used alone or in combination of two or more kinds. In the case of using a combination of two or more kinds of the above-mentioned polyoxometalate anions, the molar ratio of the tungsten to the molybdenum in the whole polyoxometalate anion is preferably in the above range.

In the second compound represented by the general formula (II), "b" is the number of molecules of the cation in the molecular association; "d" is the number of molecules of the anion in the molecular association; and each of "b" and "d" is an integer of 1 or more. For a crystal or aggregate of the second compound of the present disclosure, each of "b" and "d" is not limited to 1 and can be a natural number of 2 or more, such as a natural number of 2, 3, 4 and so on. From the viewpoint of the heat resistance, it is preferable that at least part of the second compound of the present disclosure forms a molecular association where "b"≥2. From the viewpoint of the heat resistance, it is also preferable that at least part of the second compound forms a molecular association where "d" 2.

When "b" is 2 or more, the cations present in the molecular association may be one kind of cations or may be a combination of two or more kinds of cations. When "d" is 2 or more, the anions present in the molecular association may be one kind of anions, may be a combination of two or more kinds of anions, or may be a combination of organic anions and inorganic anions.

It is also preferable that the second compound of the present disclosure is normal salt, from the point of view that problems arising from the use of acid salt, such as non-smooth dispersion or dispersion liquid gelation during storage, are prevented, and the second compound obtains high dispersibility and high dispersion stability.

<Method for Producing the Compounds>

The method for producing the first and second compounds of the present disclosure is not particularly limited. For example, the first and second compounds can be obtained by synthesizing the cation represented by the general formula (A) by a method described below, and then incorporating a desired counter anion thereinto. In the case of synthesizing the cation represented by the general formula (A) by the below-described method, substituent groups as $R^1$ to $R^7$, such as alkyl and aryl groups, may be incorporated in a compound represented by the following general formula (1) and a compound represented by the following general formula (2), or $R^1$ to $R^7$ may be hydrogen atoms in the compounds represented by the following general formulae (1) and (2) and may be substituted by a known method after the cation represented by the general formula (A) is synthesized.

(Synthesis of the Cation Represented by the General Formula (A))

As the method for producing the cation represented by the general formula (A), examples include, but are not limited to, a method for producing the cation by condensation reaction of the compounds represented by the following general formulae (1) and (2), using a chlorinating agent such as phosphorus oxychloride.

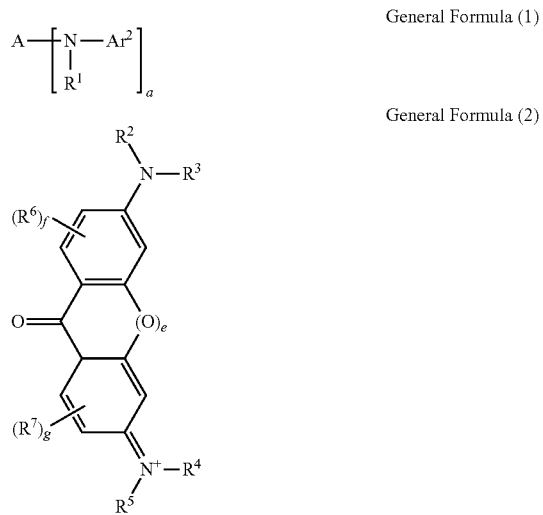

General Formula (1)

General Formula (2)

In the general formula (1), "A", $R^1$ and "a" are the same as those of the general formula (A). In the general formula (2), $R^2$, $R^3$, $R^4$, $R^5$, $R^6$, $R^7$, "e", "f" and "g" are the same as those of the general formula (A). $Ar^2$ in the general formula (1) is one in which a hydrogen atom is bound to $Ar^1$ in the general formula (A).

According to the above-mentioned synthesis method, by dehydration-condensation reaction between $Ar^2$ in the general formula (1) and the carbonyl group in the general formula (2), a triarylmethane or xanthene skeleton is formed, and the linking group "A" is introduced at the same time. Therefore, according to this synthesis method, color materials with different polymerization degrees are not formed. Also, an unreacted product, if present, contains a largely different skeleton and can be separated easily; therefore, the cation represented by the general formula (A) can be obtained in high purity and high yield.

The amount of the compound represented by the general formula (2) used in the above reaction, varies depending on the desired valence "a". For example, when "a"=2, the amount is preferably from 1.5 molar equivalent to 4.0 molar equivalent, more preferably from 1.5 molar equivalent to 3.0 molar equivalent, and still more preferably from 1.8 molar equivalent to 2.2 molar equivalent, with respect to the compound represented by the general formula (1), from the viewpoint of inhibiting the production of a by-product and increasing the reaction yield.

For the reaction, the reaction temperature is not particularly limited. In general, it is from about 110° C. to about 150° C. From the viewpoint of inhibiting a side reaction, it is preferably from 110° C. to 120° C. Also for the reaction, the reaction pressure is not particularly limited, and it is preferably from normal pressure to 0.1 MPa, and more preferably normal pressure. The reaction time may vary depending on the synthesis amount, reaction temperature, etc. It is generally in a range of from 1 hour to 10 hours, and preferably in a range of from 1 hour to 5 hours.

The amount of the added chlorinating agent such as phosphorus oxychloride, is not particularly limited. It is generally from 1.5 molar equivalent to 3.0 molar equivalent, and preferably from 1.8 molar equivalent to 3.0 molar equivalent, with respect to the compound represented by the general formula (1), from the viewpoint of increasing the reaction yield.

The compound represented by the general formula (1) may be a commercially-available product, or it can be obtained by synthesis.

The method for synthesizing the compound represented by the general formula (1) is not particularly limited. For example, it can be obtained by reacting, in a solvent, a halogenated aromatic compound containing the desired substituent group $Ar^2$ with an "a"-valent amine compound containing the desired substituent group "A", in the presence of a base and using a catalyst such as palladium acetate.

The amount of the halogenated aromatic compound used in the reaction varies depending on the desired valence "a". For example, when "a"=2, the amount is preferably from 1.5 molar equivalent to 10 molar equivalent, more preferably from 1.5 molar equivalent to 3.0 molar equivalent, and still more preferably form 1.8 molar equivalent to 2.2 molar equivalent, with respect to the amine compound, from the viewpoint of inhibiting the production of a by-product and increasing the reaction yield.

For the reaction, the reaction temperature is not particularly limited. In general, it is from about 100° C. to about 150° C. From the viewpoint of inhibiting a side reaction, it is preferably from 130° C. to 145° C. Also for the reaction, the reaction pressure is not particularly limited, and it is preferably from normal pressure to 0.1 MPa, and more preferably normal pressure. The reaction time may vary depending on the synthesis amount, reaction temperature, etc. It is generally in a range of from 6 hours to 72 hours, and preferably in a range of from 6 hours to 48 hours.

The base used in the reaction is not particularly limited. As the base, examples include, but are not limited to, sodium hydroxide, potassium hydroxide, potassium carbonate, metal alkoxide and metal amide. From the viewpoint of inhibiting a side reaction and increasing the yield of a base generator, a strong base with low nucleophilicity is preferably used, such as potassium t-butoxide, sodium t-butoxide, lithium t-butoxide, lithium diisopropylamide, potassium hexamethyldisilazide, and lithium tetramethylpiperidide. Of the strong bases with low nucleophilicity, potassium t-butoxide is more preferred.

The amount of the added base is not particularly limited. It is generally from 2.0 molar equivalent to 4.0 molar equivalent, and more preferably from 2.5 molar equivalent to 3.5 molar equivalent, with respect to the amine compound, from the viewpoint of increasing the reaction yield.

In the disclosed embodiments of the present disclosure, an intermediate represented by the following general formula (VI) is preferably used as the compound represented by the general formula (1), from the point of view that the substituent group represented by the general formula (V) can be introduced as the linking group "A" of the cation represented by the general formula (A):

General Formula (VI)

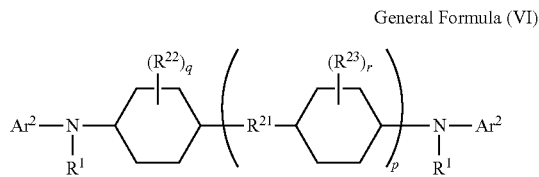

where $R^1$ is a hydrogen atom, an alkyl group optionally containing a substituent group, or an aryl group optionally containing a substituent group; $Ar^2$ is a monovalent aromatic group optionally containing a substituent group; $R^{21}$ is an alkylene group containing 1 to 3 carbon atoms and optionally containing, as a substituent group, an alkyl group containing 1 to 4 carbon atoms or an alkoxy group containing 1 to 4 carbon atoms; each of $R^{22}$ and $R^{23}$ is independently an alkyl group containing 1 to 4 carbon atoms or an alkoxy group containing 1 to 4 carbon atoms; "p" is an integer of from 1 to 3; each of "q" and "r" is independently an integer of from 0 to 4; R's may be the same or different; $Ar^2$s may be the same or different; when two or more $R^{21}$s are present, they may be the same or different; when two or more $R^{22}$s are present, they may be the same or different; when two or more $R^{23}$s are present, they may be the same or different; and when two or more "r"s are present, they may be the same or different.

In the method for synthesizing the intermediate represented by the general formula (1), the intermediate represented by the general formula (VI) can be obtained by selecting and using, as the amine compound, an amine compound represented by the following general formula (3):

General Formula (3)

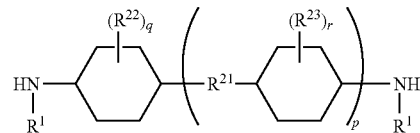

where $R^1$, $R^{21}$, $R^{22}$, $R^{23}$, "p", "q" and "r" are the same as those of the general formula (VI).

As the amine compound represented by the general formula (3), a commercially-available product can be used. As the amine compound represented by the general formula (3), examples include, but are not limited to, compounds represented by the following chemical formulae:

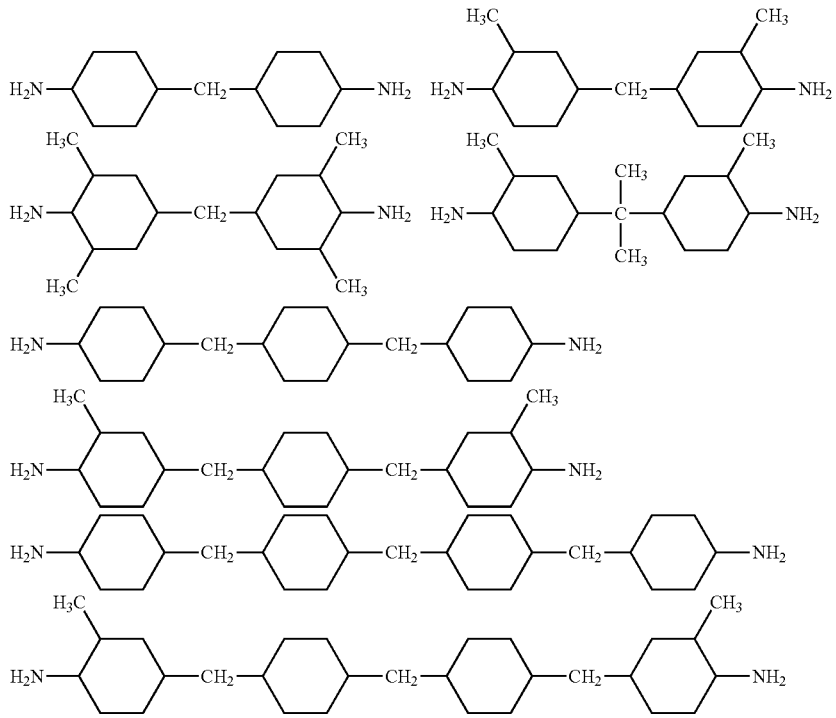

As the halogenated aromatic compound, a commercially-available product can be used, such as iodobenzene, bromobenzene, chlorobenzene, iodonaphthalene, bromonaphthalene, chloronaphthalene, bromoanthracene and chloroanthracene.

The compound represented by the general formula (2) may be a commercially-available product, or it can be obtained by synthesis.

The method for synthesizing the compound represented by the general formula (2) is not particularly limited. For example, it can be obtained by reacting, in a solvent, 4,4'-dichlorobenzophenone, 3,6-dichloroxanthone or the like with an amine compound containing a desired substituent group such as the substituent group represented by the general formula (III) or (IV), in the presence of a base and using a catalyst such as palladium acetate.

The reaction condition is not particularly limited. The compound represented by the general formula (2) can be synthesized in the same condition as the method for synthesizing the compound represented by the general formula (1).

EXAMPLES

Hereinafter, the disclosed embodiments of the present disclosure will be described in detail, by way of examples. The disclosed embodiments are not limited by the following examples.

Synthesis Example 1: Synthesis of Intermediate A-1 (Example)

First, 15.2 g (60 mmol) of 1-iodonaphthalene (manufactured by Wako Pure Chemical Industries, Ltd.), 6.31 g (30 mmol) of 4,4'-methylene bis(cyclohexylamine) (manufactured by Tokyo Chemical Industry Co., Ltd.), 8.07 g (84 mmol) of sodium t-butoxide, 0.09 g (0.2 mmol) of 2-dicyclohexylphosphino-2',6',-dimethoxybiphenyl (manufactured by Aldrich), and 0.021 g (0.1 mmol) of palladium acetate (manufactured by Wako Pure Chemical Industries, Ltd.) were dispersed in 30 mL of xylene and reacted at 130° C. to 135° C. for 48 hours. After the reaction was completed, the reaction product was cooled to room temperature and mixed with water for extraction. Next, the product thus obtained was dried and concentrated with magnesium sulfate, thereby obtaining the following intermediate A-1 in an amount of 8.5 g (yield 70%).

The compound thus obtained was confirmed to be a target compound from the following analysis results:

MS (ESI) (m/z): 407 (M+H),
Elemental analysis values: CHN measurement values (85.47%, 8.02%, 6.72%); theoretical values (85.26%, 8.11%, 6.63%)

Intermediate A-1

Synthesis Example 2: Synthesis of Intermediate A-2 (Example)

The following intermediate A-2 was obtained (yield 94%) in the same manner as Synthesis Example 1, except that 30 mmol of 4,4'-methylene bis(2-methylcyclohexylamine) (manufactured by Tokyo Chemical Industry Co., Ltd.) was used in place of the 4,4'-methylene bis(cyclohexylamine).

The compound thus obtained was confirmed to be a target compound from the following analysis results:

MS (ESI) (m/z): 491 (M+H)
Elemental analysis values: CHN measurement values (85.72%, 8.53%, 5.75%); theoretical values (85.66%, 8.63%, 5.71%)

Intermediate A-2

Synthesis Example 3: Synthesis of Intermediate A-3 (Example)

The following intermediate A-3 was obtained (yield 72%) in the same manner as Synthesis Example 1, except that 30 mmol of 4,4'-methylene bis(2,6-dimethylcyclohexylamine) (CAS No. 65962-45-0) was used in place of the 4,4'-methylene bis(cyclohexylamine).

The compound thus obtained was confirmed to be a target compound from the following analysis results:

MS (ESI) (m/z): 519 (M+H)
Elemental analysis values: CHN measurement values (85.75%, 8.86%, 5.39%); theoretical values (85.66%, 8.94%, 5.40%)

Intermediate A-3

Synthesis Example 4: Synthesis of Intermediate A-4

The following intermediate A-4 was obtained (yield 70%) in the same manner as Synthesis Example 1, except that 30 mmol of norbornane diamine (NBDA) (CAS No. 56602-77-8) (manufactured by Mitsui Chemicals, Inc.) was used in place of the 4,4'-methylene bis(cyclohexylamine).

The compound thus obtained was confirmed to be a target compound from the following analysis results:

MS (ESI) (m/z): 407 (M+H),
Elemental analysis values: CHN measurement values (85.47%, 8.02%, 6.72%); theoretical values (85.26%, 8.11%, 6.63%)

Intermediate A-4

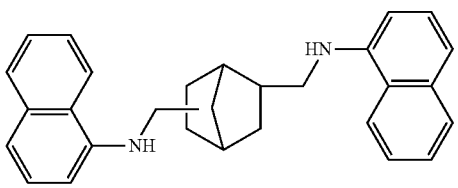

Intermediate B-2

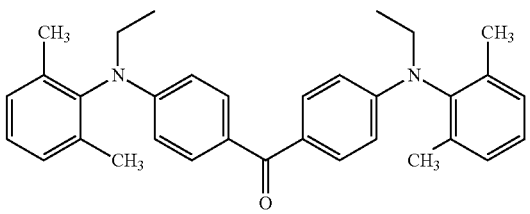

Synthesis Example 5: Synthesis of Intermediate B-1

First, 15.0 g (59.7 mmol) of 4,4'-dichlorobenzophenone (manufactured by Wako Pure Chemical Industries, Ltd.), 16.3 g (121 mmol) of N-ethyl-o-toluidine (manufactured by Wako Pure Chemical Industries, Ltd.), 16.1 g (168 mmol) of sodium t-butoxide, 2.86 g (6.0 mmol) of 2-dicyclohexyl-phosphino-2',4',6',-triisopropylbiphenyl (Xphos) (manufactured by Johnson Matthey), and 673 mg (3.0 mmol) of palladium acetate (manufactured by Wako Pure Chemical Industries, Ltd.) were dispersed in 130 mL of xylene and reacted at 100° C. to 105° C. for 20 hours. After the reaction was completed, the reaction product was cooled to room temperature and mixed with 200 ml of toluene and 200 ml of water for extraction. A toluene solution thus obtained was dried with magnesium sulfate and then concentrated under reduced pressure. A residue thus obtained was diluted with toluene and refined by silica-gel column chromatography, thereby obtaining the following intermediate B-1 in an amount of 11.8 g (yield 44%).

The compound thus obtained was confirmed to be a target compound from the following analysis results:
MS (ESI) (m/z): 449 (M+H),
Elemental analysis values: CHN measurement values (82.90%, 7.33%, 6.22%); theoretical values (82.81%, 7.40%, 6.23%)

Intermediate B-1

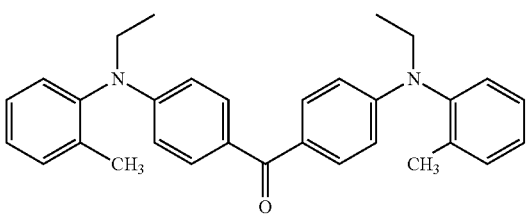 [SMILES: CCN(c1ccc(C(=O)c2ccc(N(CC)c3ccccc3C)cc2)cc1)c1ccccc1C]

Synthesis Example 6: Synthesis of Intermediate B-2

The following intermediate B-2 was obtained (yield 52%) in the same manner as Synthesis Example 5, except that N-ethyl-2,6-dimethylaniline was used in place of the N-ethyl-o-toluidine (manufactured by Wako Pure Chemical Industries, Ltd.)

The compound thus obtained was confirmed to be a target compound from the following analysis results:
MS (ESI) (m/z): 477 (M+H),
Elemental analysis values: CHN measurement values (83.23%, 7.55%, 5.84%); theoretical values (83.15%, 7.61%, 5.88%)

Synthesis Example 7: Synthesis of Intermediate B-3

The following intermediate B-3 was obtained (yield 51%) in the same manner as Synthesis Example 5, except that N-ethyl-2,4,6-trimethylaniline was used in place of the N-ethyl-o-toluidine (manufactured by Wako Pure Chemical Industries, Ltd.)

The compound thus obtained was confirmed to be a target compound from the following analysis results:
MS (ESI) (m/z): 505 (M+H),
Elemental analysis values: CHN measurement values (83.39%, 7.91%, 5.54%); theoretical values (83.29%, 7.99%, 5.55%)

Intermediate B-3

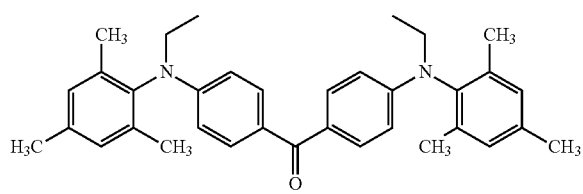

Synthesis Example 8: Synthesis of Intermediate B-4

The following intermediate B-4 was obtained (yield 71%) in the same manner as Synthesis Example 5, except that N-ethyl-2-methylcyclohexylamine was used in place of the N-ethyl-o-toluidine (manufactured by Wako Pure Chemical Industries, Ltd.)

The compound thus obtained was confirmed to be a target compound from the following analysis results:
MS (ESI) (m/z): 461 (M+H),
Elemental analysis values: CHN measurement values (80.89%, 9.60%, 6.05%); theoretical values (80.82%, 9.63%, 6.08%)

Intermediate B-4

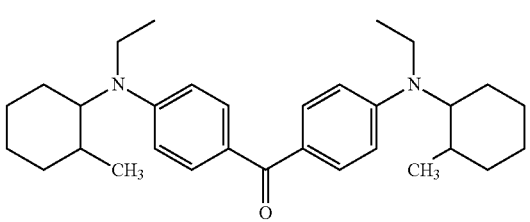 [SMILES: CCN(c1ccc(C(=O)c2ccc(N(CC)C3CCCCC3C)cc2)cc1)C1CCCCC1C]

Example 1-1: Synthesis of Compound 1-1

First, 2.47 g (6.08 mmol) of the intermediate A-4 obtained in Synthesis Example 4, 6.00 g (13.4 mmol) of the intermediate B-1 obtained in Synthesis Example 5, and 10 mL of chlorobenzene were mixed and stirred at 45° C. to 50° C. Then, 2.06 g (13.4 mmol) of phosphorus oxychloride (manufactured by Wako Pure Chemical Industries, Ltd.) was added thereto in a dropwise manner. The mixture was stirred at 45° C. to 50° C. for 20 hours. After a reaction was completed, 100 ml of chloroform and 100 mL of water were added to dissolve the reacted mixture. A chloroform layer thus formed was separated therefrom, washed with water, dried with magnesium sulfate and then concentrated under reduced pressure. A residue thus obtained was diluted with chloroform and refined by silica-gel column chromatography, thereby obtaining the following compound 1-1 in an amount of 7.5 g (yield 91%).

The compound thus obtained was confirmed to be a target compound from the following analysis results:

MS (ESI) (m/z): 635(+), divalent

Elemental analysis values: CHN measurement values (81.59%, 6.85%, 5.25%); theoretical values (81.53%, 6.92%, 5.29%)

Compound 1-1

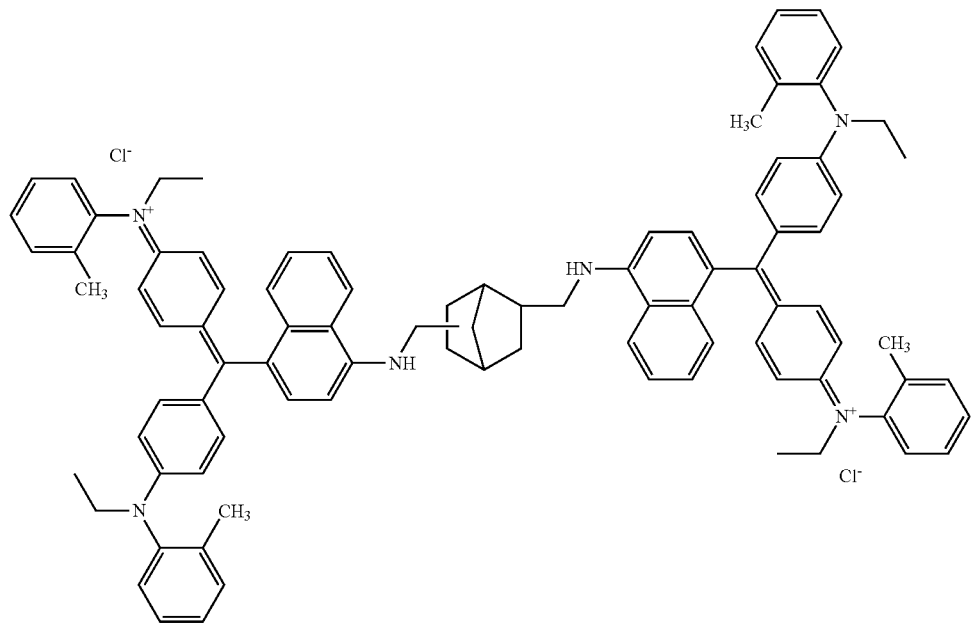 [SMILES: CCNc1ccc(C(=C2C=CC(=[N+](CC)c3ccccc3C)C=C2)c2ccc(N(CC)c3ccccc3C)cc2)c2ccccc12 ; [Cl-] ; CCN(c1ccc(C(=C2C=CC(=[N+](CC)c3ccccc3C)C=C2)c2ccc(NCC3CC4CCC3C4)c3ccccc23)cc1)c1ccccc1C ; [Cl-]]

Example 1-2: Synthesis of Compound 1-2

The following compound 1-2 was obtained (yield 82%) in the same manner as Example 1-1, except that the intermediate A-1 of Synthesis Example 1 was used in place of the intermediate A-4.

The compound thus obtained was confirmed to be a target compound from the following analysis results:

MS (ESI) (m/z): 663(+), divalent

Elemental analysis values: CHN measurement values (81.75%, 7.17%, 5.99%); theoretical values (81.69%, 7.22%, 6.02%)

Compound 1-2

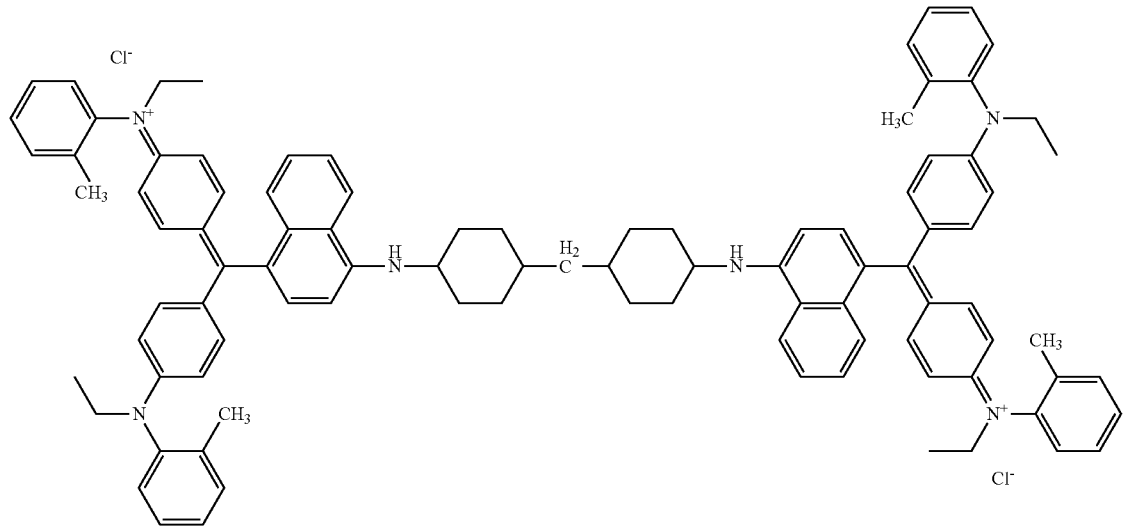 [SMILES: CCN(c1ccc(C(=C2C=CC(=[N+](CC)c3ccccc3C)C=C2)c2ccc(NC3CCC(CC4CCC(Nc5ccc(C(=C6C=CC(=[N+](CC)c7ccccc7C)C=C6)c6ccc(N(CC)c7ccccc7C)cc6)c6ccccc56)CC4)CC3)c3ccccc23)cc1)c1ccccc1C ; [Cl-] ; [Cl-]]

Example 1-3: Synthesis of Compound 1-3

The following compound 1-3 was obtained (yield 87%) in the same manner as Example 1-1, except that the intermediate A-2 of Synthesis Example 2 was used in place of the intermediate A-4.

The compound thus obtained was confirmed to be a target compound from the following analysis results:

MS (ESI) (m/z): 677(+), divalent

Elemental analysis values: CHN measurement values (81.81%, 7.31%, 5.85%); theoretical values (81.77%, 7.36%, 5.90%)

Compound 1-3

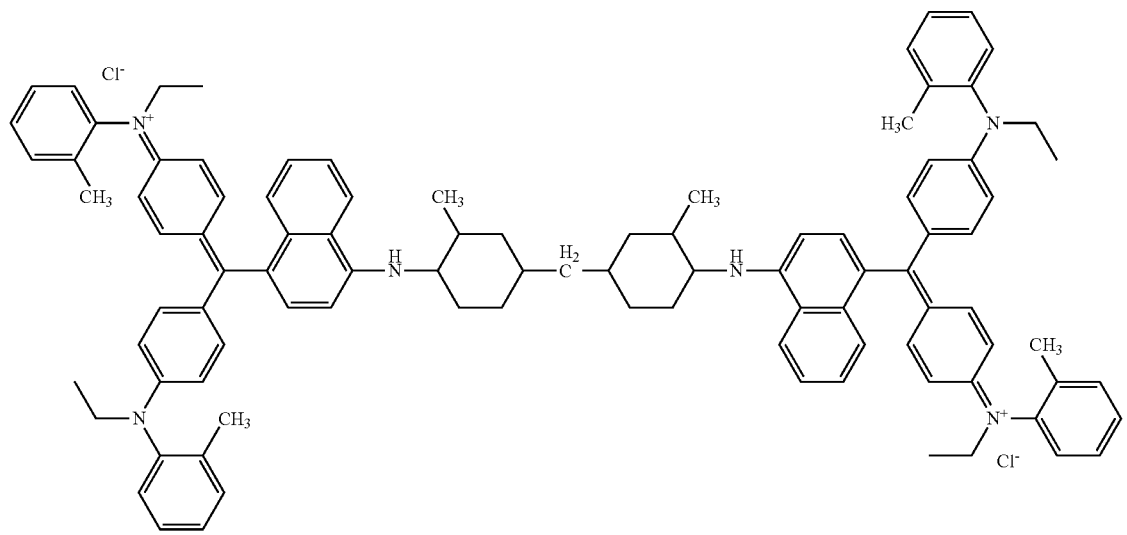 [SMILES: CCN(c1ccc(C(=C2C=CC(=[N+](CC)c3ccccc3C)C=C2)c2ccc(NC3CCC(CC4CCC(Nc5ccc(C(=C6C=CC(=[N+](CC)c7ccccc7C)C=C6)c6ccc(N(CC)c7ccccc7C)cc6)c6ccccc56)C(C)C4)CC3C)c3ccccc23)cc1)c1ccccc1C ; [Cl-] ; [Cl-]]

Example 1-4: Synthesis of Compound 1-4

The following compound 1-4 was obtained (yield 52%) in the same manner as Example 1-1, except that the intermediate A-1 of Synthesis Example 1 was used in place of the intermediate A-4, and 4,4'-bis(diethylamino)benzophenone (manufactured by Tokyo Chemical Industry Co., Ltd.) was used in place of the intermediate B-1.

The compound thus obtained was confirmed to be a target compound from the following analysis results:

MS (ESI) (m/z): 538(+), divalent

Elemental analysis values: CHN measurement values (73.51%, 8.02%, 7.28%); theoretical values (78.43%, 8.07%, 7.32%)

Compound 1-4

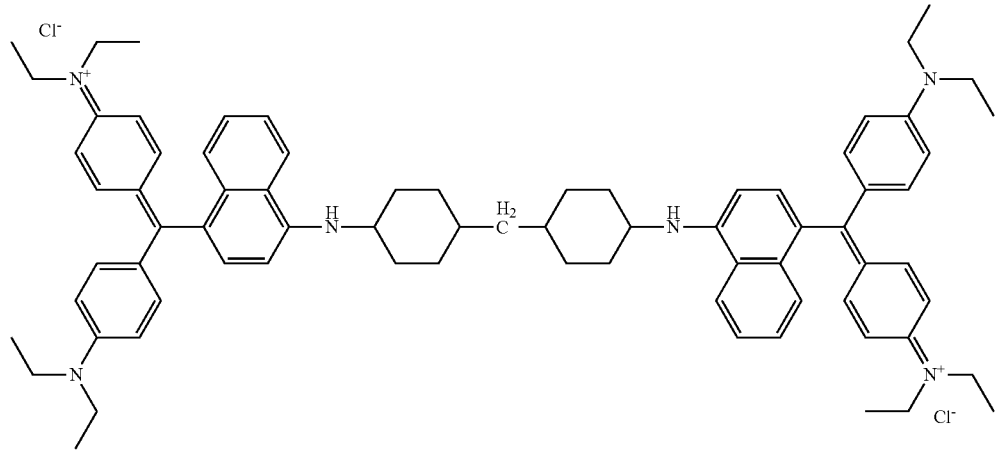 [SMILES: CCN(CC)c1ccc(C(=C2C=CC(=[N+](CC)CC)C=C2)c2ccc(NC3CCC(CC4CCC(Nc5ccc(C(=C6C=CC(=[N+](CC)CC)C=C6)c6ccc(N(CC)CC)cc6)c6ccccc56)CC4)CC3)c3ccccc23)cc1 ; [Cl-] ; [Cl-]]

Example 1-5: Synthesis of Compound 1-5

The following compound 1-5 was obtained (yield 65%) in the same manner as Example 1-1, except that the intermediate A-2 of Synthesis Example 2 was used in place of the intermediate A-4, and 4,4'-bis(diethylamino)benzophenone (manufactured by Tokyo Chemical Industry Co., Ltd.) was used in place of the intermediate B-1.

The compound thus obtained was confirmed to be a target compound from the following analysis results:

MS (ESI) (m/z): 552(+), divalent

Elemental analysis values: CHN measurement values (78.68%, 8.17%, 7.10%); theoretical values (78.61%, 8.22%, 7.14%)

Compound 1-5

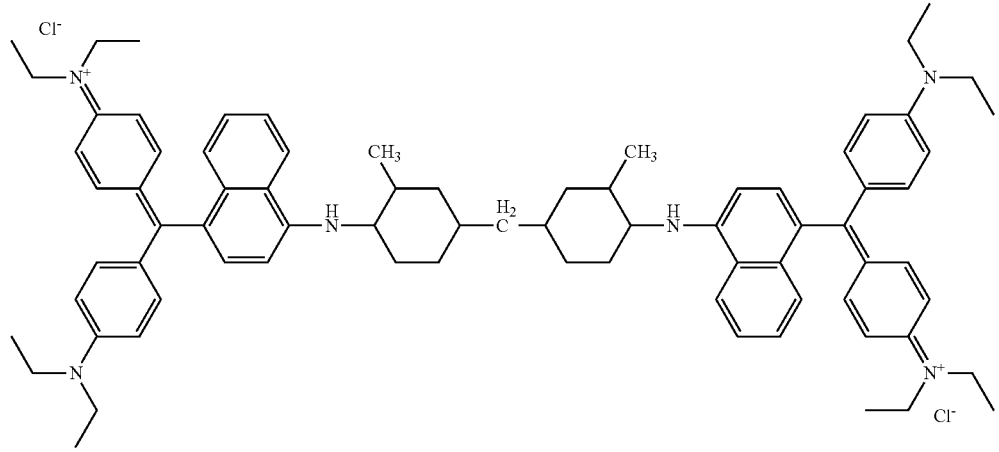 [SMILES: CCN(CC)c1ccc(C(=C2C=CC(=[N+](CC)CC)C=C2)c2ccc(NC3CCC(CC4CCC(Nc5ccc(C(=C6C=CC(=[N+](CC)CC)C=C6)c6ccc(N(CC)CC)cc6)c6ccccc56)C(C)C4)CC3C)c3ccccc23)cc1 ; [Cl-] ; [Cl-]]

Example 1-6: Synthesis of Compound 1-6

The following compound 1-6 was obtained (yield 76%) in the same manner as Example 1-1, except that the intermediate A-3 of Synthesis Example 3 was used in place of the intermediate A-4.

The compound thus obtained was confirmed to be a target compound from the following analysis results:

MS (ESI) (m/z): 691(+), divalent

Elemental analysis values: CHN measurement values (81.91%, 7.44%, 5.72%); theoretical values (81.84%, 7.49%, 5.78%)

Compound 1-6

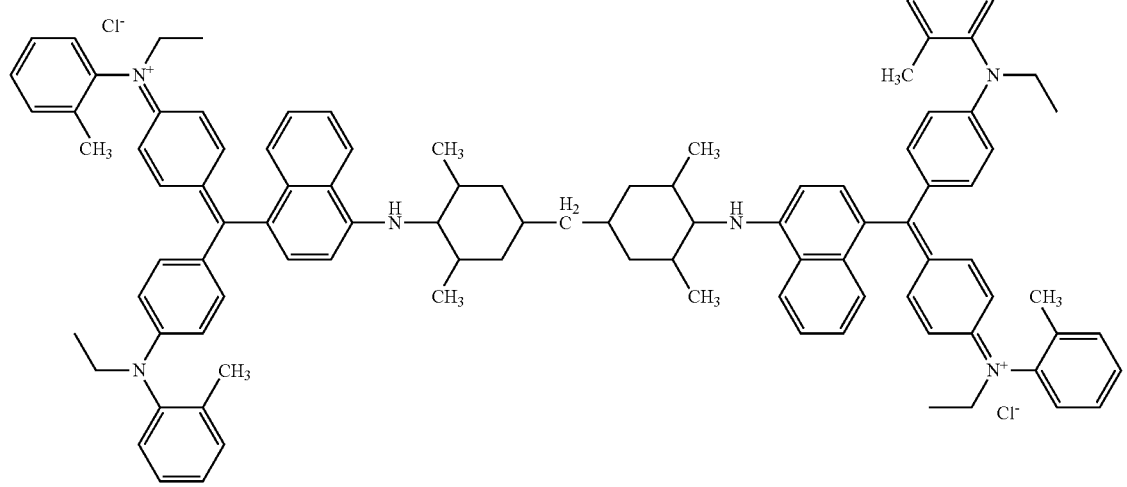

Example 1-7: Synthesis of Compound 1-7

The following compound 1-7 was obtained (yield 81%) in the same manner as Example 1-1, except that the intermediate A-1 of Synthesis Example 1 was used in place of the intermediate A-4, and the intermediate B-2 of Synthesis Example 6 was used in place of the intermediate B-1.

The compound thus obtained was confirmed to be a target compound from the following analysis results:

MS (ESI) (m/z): 691(+), divalent

Elemental analysis values: CHN measurement values (81.90%, 7.44%, 5.74%); theoretical values (81.84%, 7.49%, 5.78%)

Compound 1-7

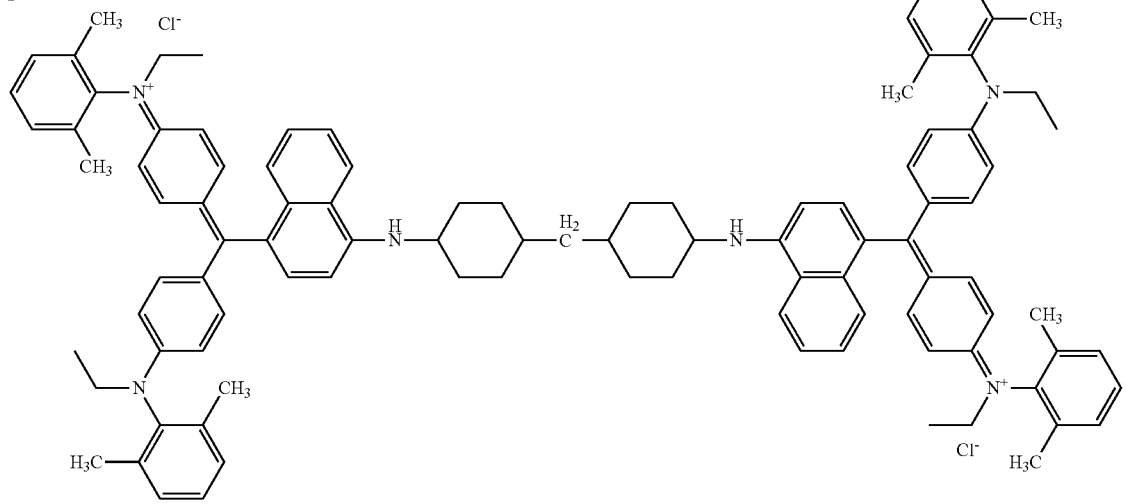

Example 1-8: Synthesis of Compound 1-8

The following compound 1-8 was obtained (yield 73%) in the same manner as Example 1-1, except that the intermediate A-1 of Synthesis Example 1 was used in place of the intermediate A-4, and the intermediate B-3 of Synthesis Example 7 was used in place of the intermediate B-1.

The compound thus obtained was confirmed to be a target compound from the following analysis results:
MS (ESI) (m/z): 719(+), divalent
Elemental analysis values: CHN measurement values (81.97%, 7.55%, 5.65%); theoretical values (81.91%, 7.62%, 5.67%)

Compound 1-8

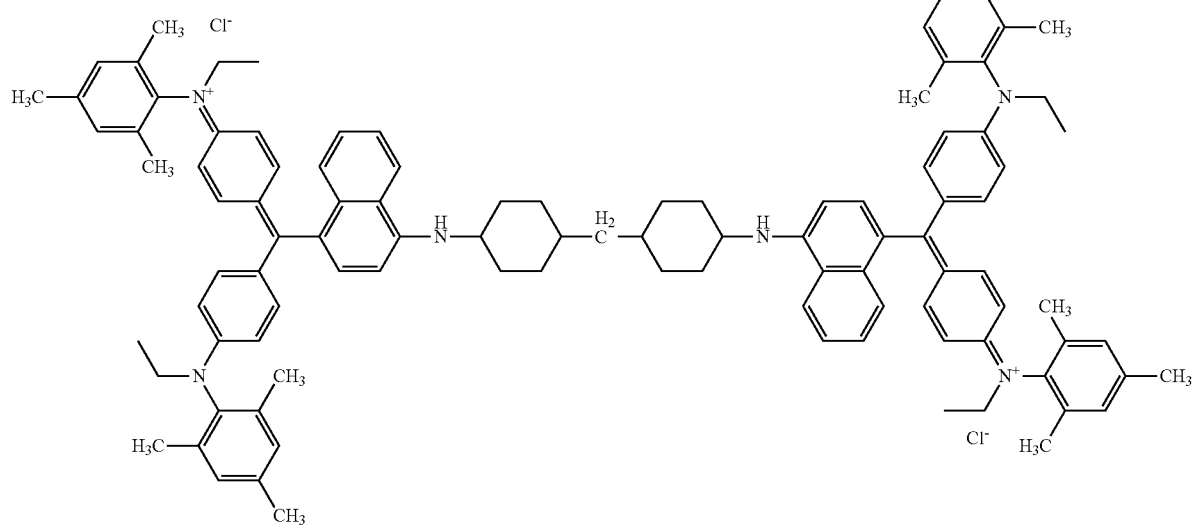

Example 1-9: Synthesis of Compound 1-9

The following compound 1-9 was obtained (yield 71%) in the same manner as Example 1-1, except that the intermediate A-1 of Synthesis Example 1 was used in place of the intermediate A-4, and the intermediate B-4 of Synthesis Example 8 was used in place of the intermediate B-1.

The compound thus obtained was confirmed to be a target compound from the following analysis results:
MS (ESI) (m/z): 675(+), divalent
Elemental analysis values: CHN measurement values (80.38%, 8.73%, 5.85%); theoretical values (80.30%, 8.80%, 5.91%)

Compound 1-9

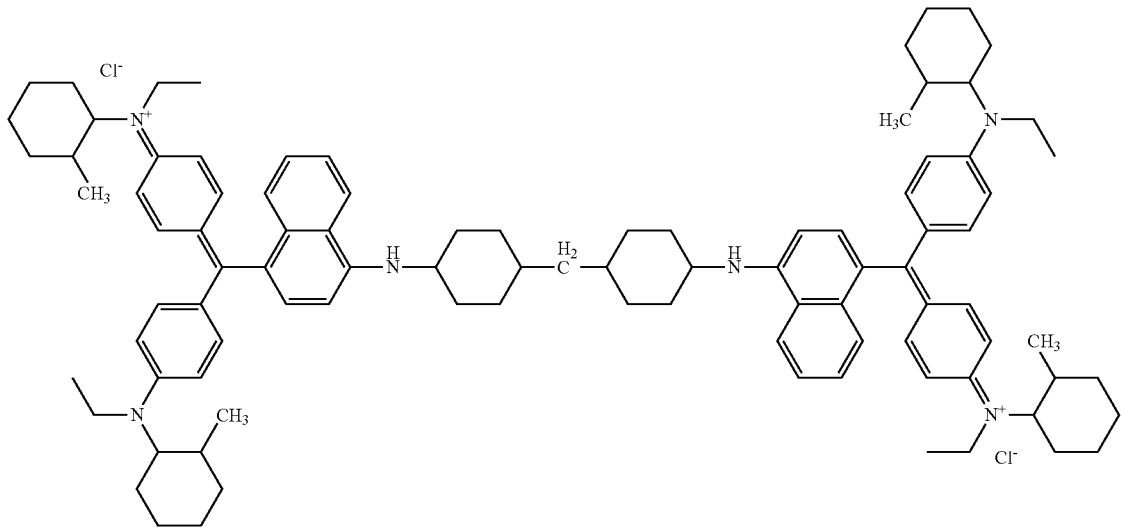 [SMILES: CCN(c1ccc(C(=C2C=CC(=[N+](CC)C3CCCCC3C)C=C2)c2ccc(NC3CCC(CC4CCC(Nc5ccc(C(=C6C=CC(=[N+](CC)C7CCCCC7C)C=C6)c6ccc(N(CC)C7CCCCC7C)cc6)c6ccccc56)CC4)CC3)c3ccccc23)cc1)C1CCCCC1C ; [Cl-] ; [Cl-]]

Comparative Example 1: Synthesis of Compound 1-X

First, 8.46 g (20.8 mmol) of the intermediate A-4 of Synthesis Example 4, 13.5 g (41.6 mmol) of 4,4'-bis(dimethylamino)benzophenone (manufactured by Tokyo Chemical Industry Co., Ltd.) and 60 mL of toluene were mixed and stirred at 45° C. to 50° C. Then, 6.38 g (51.5 mmol) of phosphorus oxychloride (manufactured by Wako Pure Chemical Industries, Ltd.) was added thereto in a dropwise manner. The mixture was refluxed for two hours and cooled down. After a reaction was completed, the toluene was decanted. A resinous precipitate thus obtained was mixed with concentrated hydrochloric acid, 40 mL of chloroform and 40 mL of water and dissolved. A chloroform layer thus formed was separated therefrom, washed with water, and then dried and concentrated with magnesium sulfate. A concentrate thus obtained was mixed with 65 mL of ethyl acetate and refluxed. After cooling the resultant product, a precipitate thus formed was obtained by filtration, thereby obtaining the following compound 1-X in an amount of 15.9 g (yield 70%).

The compound thus obtained was confirmed to be a target compound from the following analysis results:
MS (ESI) (m/z): 511(+), divalent
Elemental analysis values: CHN measurement values (78.13%, 7.48%, 7.78%); theoretical values (78.06%, 7.75%, 7.69%)

Compound 1-X

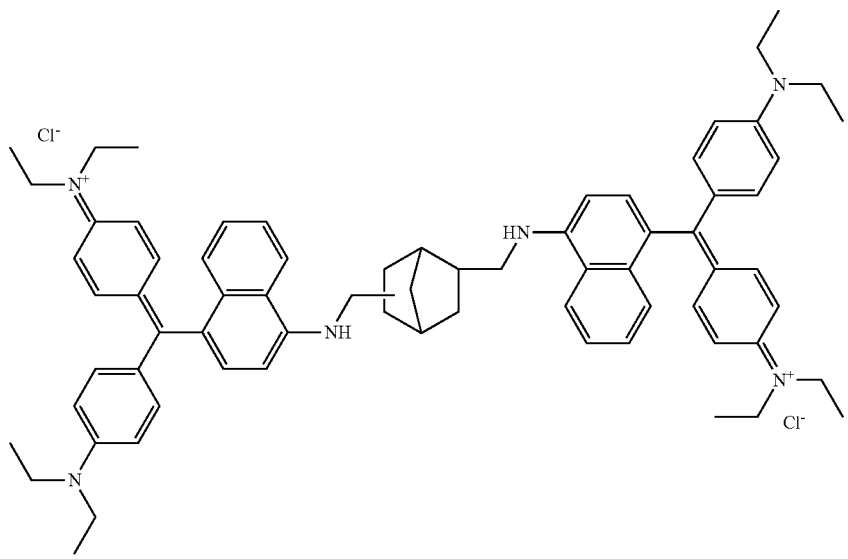 [SMILES: CCNc1ccc(C(=C2C=CC(=[N+](CC)CC)C=C2)c2ccc(N(CC)CC)cc2)c2ccccc12 ; [Cl-] ; CCN(CC)c1ccc(C(=C2C=CC(=[N+](CC)CC)C=C2)c2ccc(NCC3CC4CCC3C4)c3ccccc23)cc1 ; [Cl-]]

Example 2-1: Synthesis of Compound 2-1

First, 2.59 g (0.76 mmol) of 12-tungstophosphoric acid n-hydrate (manufactured by Kanto Chemical Co., Inc.) was dissolved in a mixed solution of 40 mL of methanol and 40 mL of water, by heating. Then, 1.6 g (1.19 mmol) of the compound 1-1 was added to the solution, and the mixture was stirred for one hour. A precipitate thus formed was obtained by filtration and washed with water. The thus-obtained precipitate was dried under reduced pressure, thereby obtaining the following compound 2-1 in an amount of 3.4 g (yield 95%).

The compound thus obtained was confirmed to be a target compound from the following analysis results:

31P NMR (d-dmso, ppm) δ–15.15

MS (MALDI) (m/z): 1270 ($M^+$), 2879 ($MH_2^-$)

Elemental analysis values: CHN measurement values (35.01%, 2.88%, 2.59%); theoretical values (34.29%, 2.91%, 2.64%)

Fluorescent X-ray analysis: Mo/W measurement values (0%, 100%); theoretical values (0%, 100%)

Compound 2-1

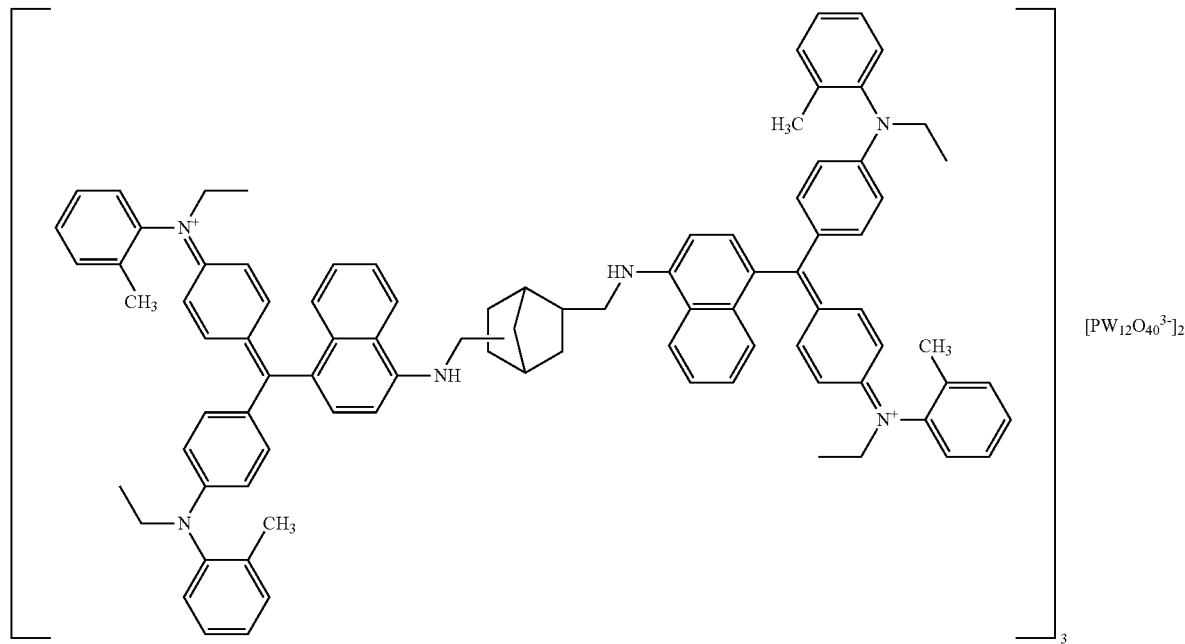

Example 2-2: Synthesis of Compound 2-2

The following compound 2-2 was obtained (yield 96%) in the same manner as Example 2-1, except that the compound 1-2 was used in place of the compound 1-1.

The compound thus obtained was confirmed to be a target compound from the following analysis results:

31P NMR (d-dmso, ppm) δ–15.15

MS (MALDI) (m/z): 1326 ($M^+$), 2879 ($MH_2^-$)

Elemental analysis values: CHN measurement values (35.28%, 3.15%, 2.63%); theoretical values (35.18%, 3.11%, 2.59%)

Fluorescent X-ray analysis: Mo/W measurement values (0%, 100%); theoretical values (0%, 100%)

Compound 2-2

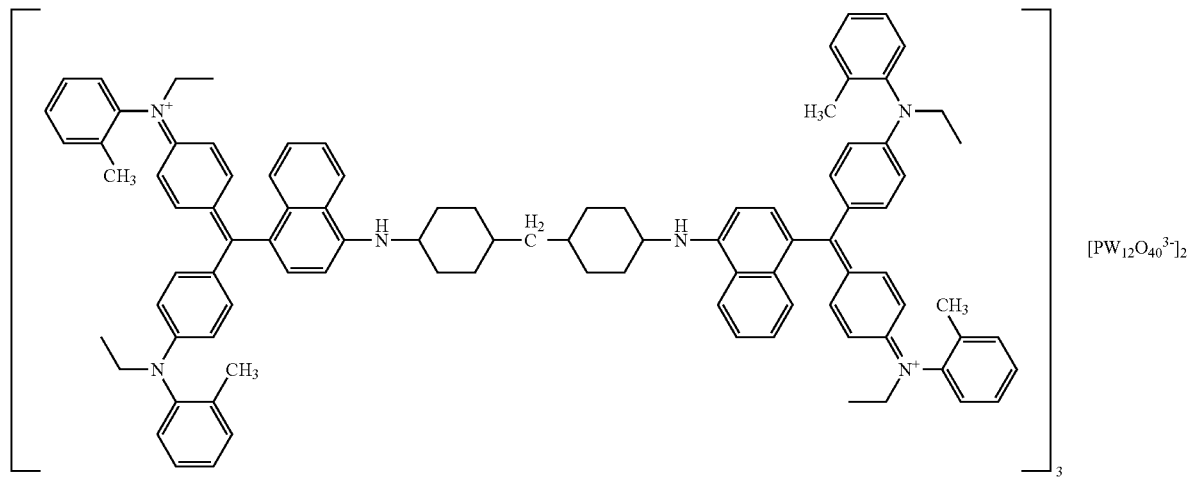

Example 2-3: Synthesis of Compound 2-3

The following compound 2-3 was obtained (yield 95%) in the same manner as Example 2-1, except that the compound 1-3 was used in place of the compound 1-1.

The compound thus obtained was confirmed to be a target compound from the following analysis results:
31P NMR (d-dmso, ppm) δ−15.15
MS (MALDI) (m/z): 1355 (M$^+$), 2879 (MH$_2^+$)
Elemental analysis values: CHN measurement values (35.55%, 3.24%, 2.61%); theoretical values (35.61%, 3.20%, 2.57%)
Fluorescent X-ray analysis: Mo/W measurement values (0%, 100%); theoretical values (0%, 100%)

Compound 2-3

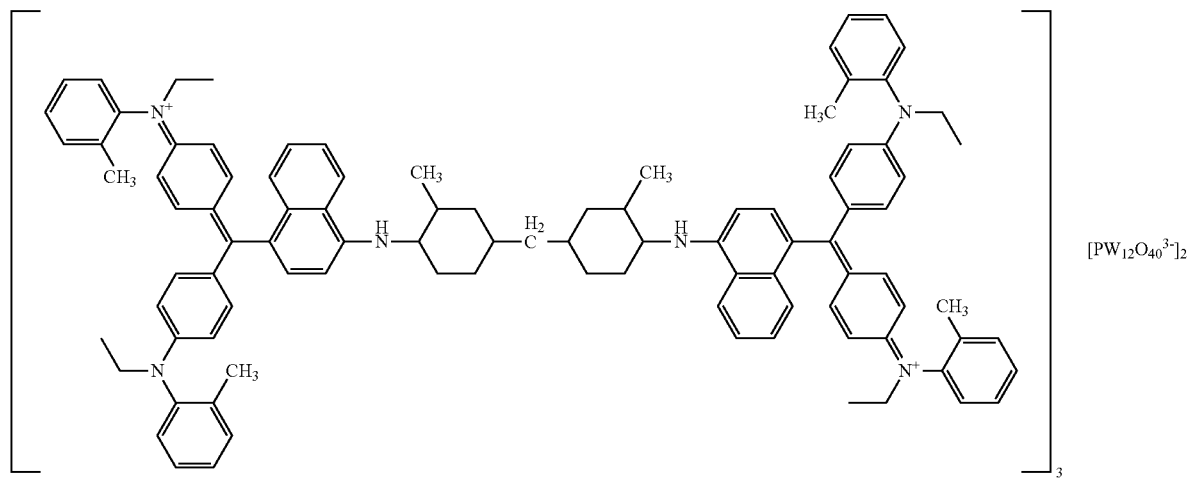

Example 2-4: Synthesis of Compound 2-4

The following compound 2-4 was obtained (yield 97%) in the same manner as Example 2-1, except that the compound 1-4 was used in place of the compound 1-1.

The compound thus obtained was confirmed to be a target compound from the following analysis results:
- 31P NMR (d-dmso, ppm) δ−15.15
- MS (MALDI) (m/z): 1078 ($M^+$), 2879 ($MH_2^-$)
- Elemental analysis values: CHN measurement values (30.20%, 3.14%, 2.86%); theoretical values (30.07%, 3.10%, 2.81%)
- Fluorescent X-ray analysis: Mo/W measurement values (0%, 100%); theoretical values (0%, 100%)

Compound 2-4

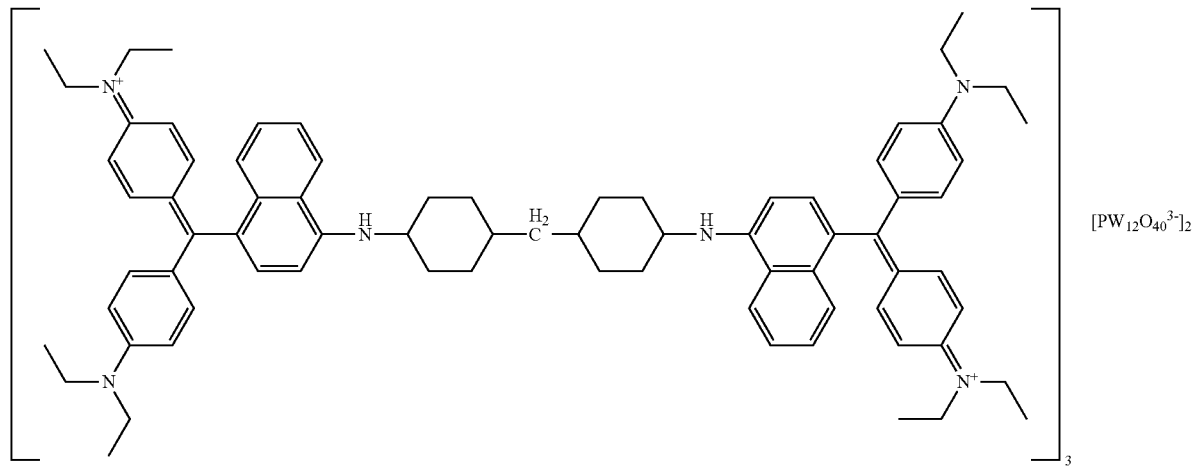

Example 2-5: Synthesis of Compound 2-5

The following compound 2-5 was obtained (yield 97%) in the same manner as Example 2-1, except that the compound 1-5 was used in place of the compound 1-1.

The compound thus obtained was confirmed to be a target compound from the following analysis results:
- 31P NMR (d-dmso, ppm) δ−15.15
- MS (MALDI) (m/z): 1106 ($M^+$), 2879 ($MH_2^-$)
- Elemental analysis values: CHN measurement values (30.63%, 3.18%, 2.75%); theoretical values (30.59%, 3.20%, 2.78%)
- Fluorescent X-ray analysis: Mo/W measurement values (0%, 100%); theoretical values (0%, 100%)

Compound 2-5

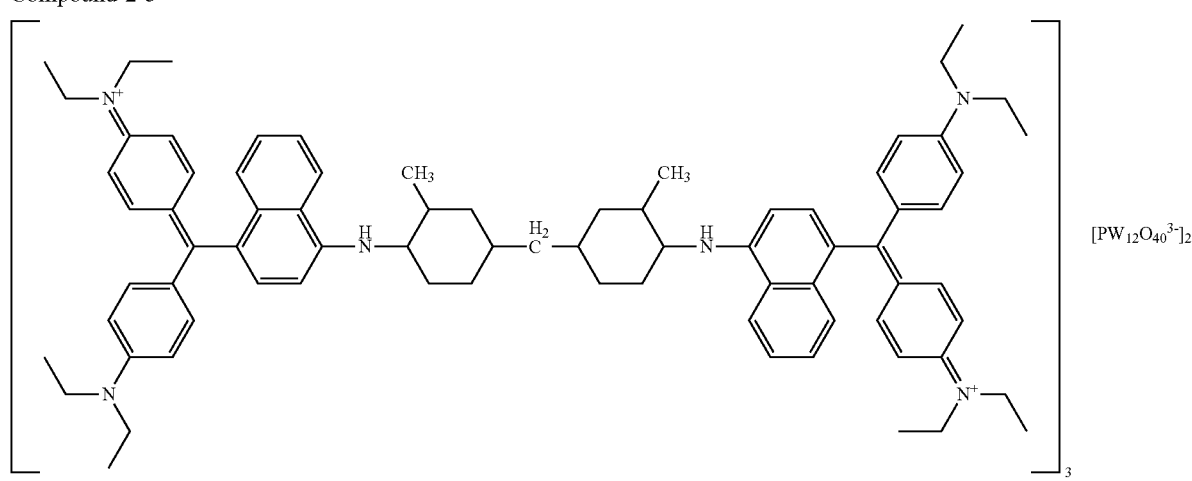

Example 2-6: Synthesis of Compound 2-6

The following compound 2-6 was obtained (yield 96%) in the same manner as Example 2-1, except that the compound 1-6 was used in place of the compound 1-1.

The compound thus obtained was confirmed to be a target compound from the following analysis results:

31P NMR (d-dmso, ppm) δ−15.15

MS (MALDI) (m/z): 1383 ($M^+$), 2879 ($MH_2^-$)

Elemental analysis values: CHN measurement values (36.25%, 3.33%, 2.54%); theoretical values (36.04%, 3.30%, 2.55%)

Fluorescent X-ray analysis: Mo/W measurement values (0%, 100%); theoretical values (0%, 100%)

Compound 2-6

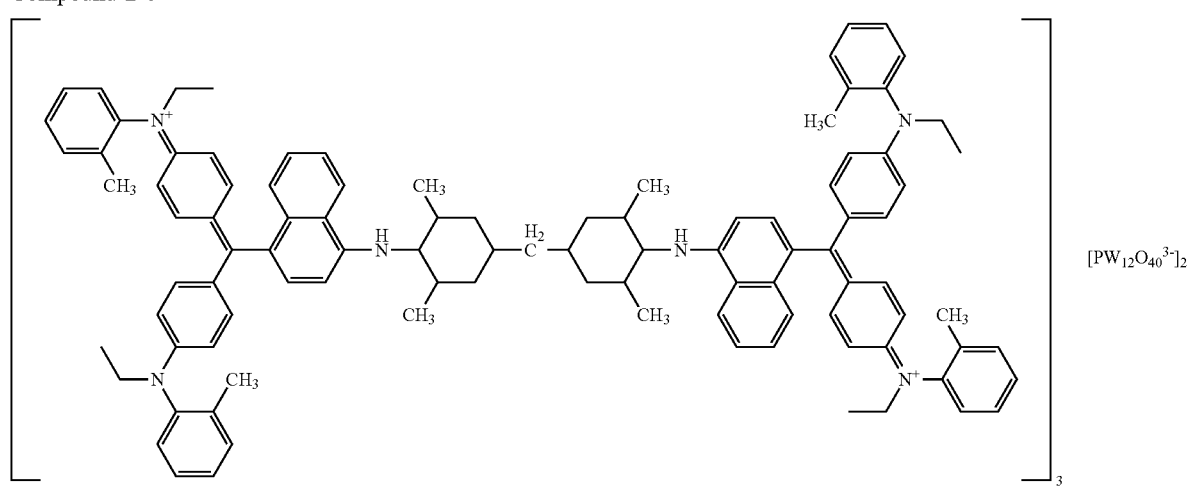

Example 2-7: Synthesis of Compound 2-7

The following compound 2-7 was obtained (yield 95%) in the same manner as Example 2-1, except that the compound 1-7 was used in place of the compound 1-1.

The compound thus obtained was confirmed to be a target compound from the following analysis results:

31P NMR (d-dmso, ppm) δ−15.15

MS (MALDI) (m/z): 1383 ($M^+$), 2879 ($MH_2^-$)

Elemental analysis values: CHN measurement values (36.25%, 3.33%, 2.54%); theoretical values (36.04%, 3.30%, 2.55%)

Fluorescent X-ray analysis: Mo/W measurement values (0%, 100%); theoretical values (0%, 100%)

Compound 2-7

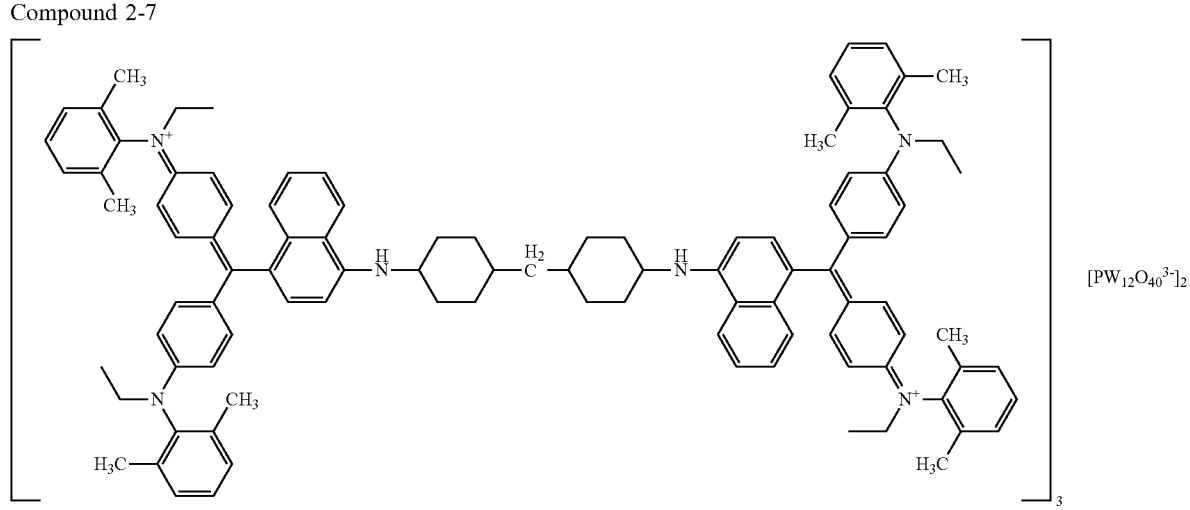

Example 2-8: Synthesis of Compound 2-8

The following compound 2-8 was obtained (yield 97%) in the same manner as Example 2-1, except that the compound 1-8 was used in place of the compound 1-1.

The compound thus obtained was confirmed to be a target compound from the following analysis results:

31P NMR (d-dmso, ppm) δ−15.15
MS (MALDI) (m/z): 1440 (M$^+$), 2879 (MH$_2^-$)
Elemental analysis values: CHN measurement values (36.88%, 3.49%, 2.51%); theoretical values (36.87%, 3.48%, 2.50%)
Fluorescent X-ray analysis: Mo/W measurement values (0%, 100%); theoretical values (0%, 100%)

Compound 2-8

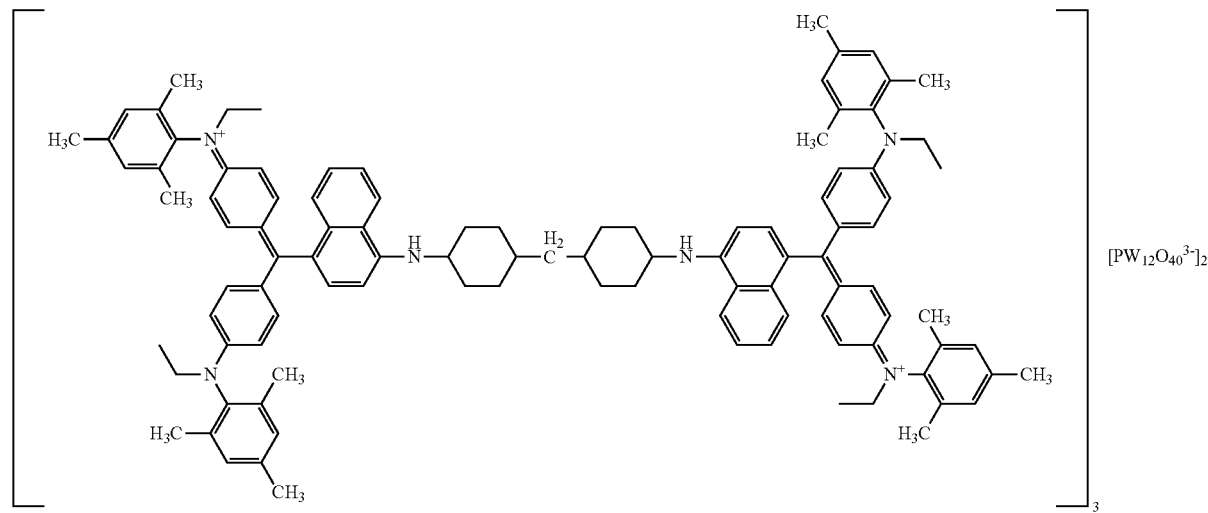

Example 2-9: Synthesis of Compound 2-9

The following compound 2-9 was obtained (yield 97%) in the same manner as Example 2-1, except that the compound 1-9 was used in place of the compound 1-1.

The compound thus obtained was confirmed to be a target compound from the following analysis results:

31P NMR (d-dmso, ppm) δ−15.15
MS (MALDI) (m/z): 1352 (M$^+$), 2879 (MH$_2^-$)
Elemental analysis values: CHN measurement values (34.88%, 3.79%, 2.58%); theoretical values (34.92%, 3.83%, 2.57%)
Fluorescent X-ray analysis: Mo/W measurement values (0%, 100%); theoretical values (0%, 100%)

Compound 2-9

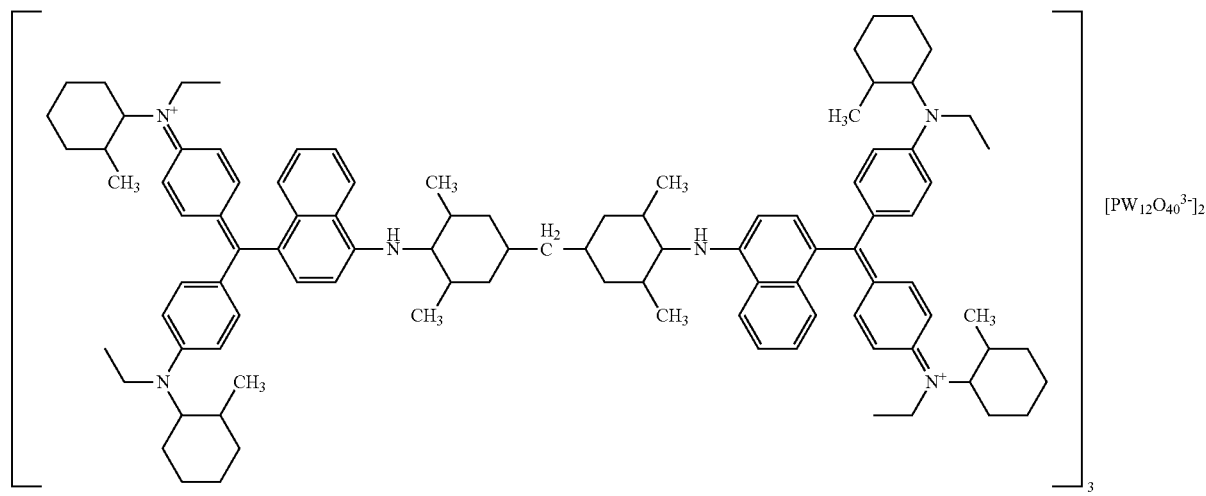

Comparative Example 2: Synthesis of Compound 2-X

The following compound 2-X was obtained (yield 97%) in the same manner as Example 2-1, except that the compound 1-X was used in place of the compound 1-1.

The compound thus obtained was confirmed to be a target compound from the following analysis results:

31P NMR (d-dmso, ppm) δ−15.15

MS (MALDI) (m/z): 1122 (M$^+$), 2879 (MH$_2^-$)

Elemental analysis values: CHN measurement values (29.04%, 2.90%, 2.81%); theoretical values (29.01%, 2.88%, 2.85%)

Fluorescent X-ray analysis: Mo/W measurement values (0%, 100%); theoretical values (0%, 100%)

Compound 2-X

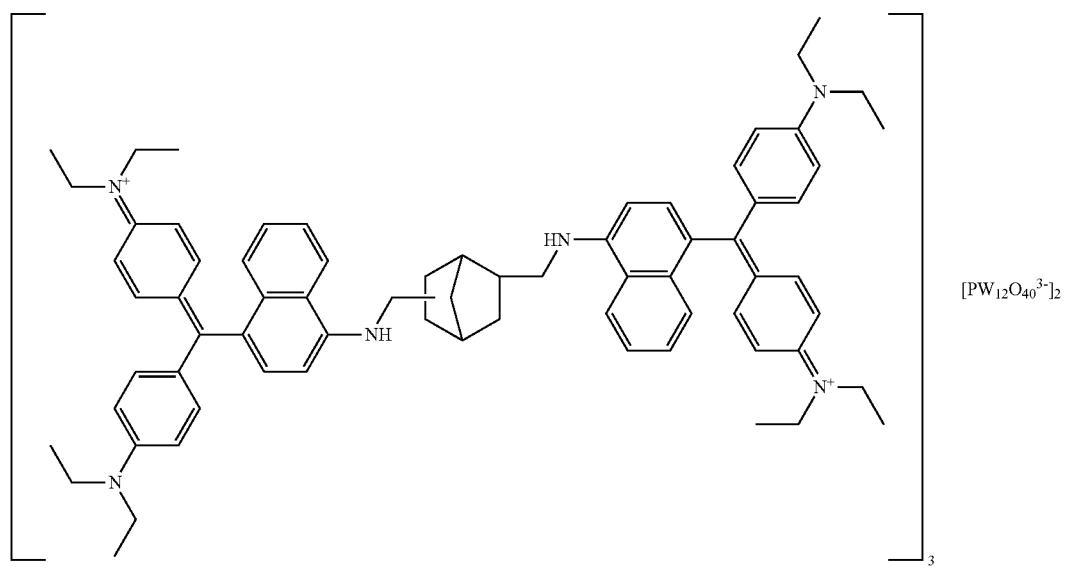

<Heat Resistance Evaluation 1>

The compounds of Examples 1-1 to 1-9 and Comparative Example 1 (about 5 mg each) were separately put in quartz pans and measured with differential thermogravimetric analyzer (TG-DTA) TG8120 (product name, manufactured by Rigaku Corporation) at a temperature increase rate of 10° C./min, up to 600° C., placing alumina in each quartz pan as a reference.

As an indicator of heat resistance, a temperature at which a weight loss of 5% occurred ($T_{5\ wt\ \%}$) was calculated for each compound. The higher the temperature at which a weight loss of 5% occurred ($T_{5\ wt\ \%}$), the better the heat resistance. The results are shown in Table 1.

<Evaluation of Post-Dyeing Fixability>

Each of the compounds of Examples 1-1 to 1-9 and Comparative Example 1 was dissolved in methanol to prepare 2 wt % methanol solutions of the compounds. A drop of each methanol solution was put on a commercially-available cotton cloth so as not to overlap with other drops. The cloth was left to stand for 30 minutes at room temperature, thereby drying the drops. Then, for each dropped solution, the diameter of a circular dyed area on the cloth was measured and determined as the pre-test dyed area diameter "A". This cloth was put in a constant temperature and humidity chamber (product name: IG420, manufactured by: Yamato Scientific Co., Ltd.) and subjected to exposure at a temperature of 80° C. and a humidity of 70% for two hours. The cloth was removed from the constant temperature and humidity chamber, and the diameter of each dyed area was measured again and determined as a post-test dyed area diameter "B". A fixability index "C" was obtained by the following formula (1) and from the difference between the dyed area diameters "A" and "B" before and after the test. The smaller the fixability index "C", the higher the post-dyeing fixability at high temperature and high humidity. The results are shown in Table 1.

$$C=(B-A)/A\times100 \quad \text{Formula (1)}$$

TABLE 1

| | Heat resistance evaluation $T_{5\ wt\%}$ (° C.) | Fixability index |
|---|---|---|
| Example 1-1 | 240 | 0 |
| Example 1-2 | 241 | 0 |
| Example 1-3 | 258 | 0 |
| Example 1-4 | 235 | 15 |
| Example 1-5 | 240 | 5 |
| Example 1-6 | 260 | 0 |
| Example 1-7 | 245 | 0 |
| Example 1-8 | 247 | 0 |
| Example 1-9 | 242 | 0 |
| Comparative Example 1 | 230 | 138 |

[Conclusion]

From the results shown in Table 1, it was revealed that the compound of the disclosed embodiments of the present disclosure has excellent heat resistance and excellent post-dyeing fixability, which is a compound represented by the general formula (I) wherein the compound contains at least one of the following structures (i) and (ii):

(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain.

(ii) At least one of $R^2$, $R^3$, $R^4$ and $R^5$ is a cycloalkyl group optionally containing a substituent group or an aryl group optionally containing a substituent group.

<Heat Resistance Evaluation 2>

The compounds of Examples 2-1 to 2-9 and Comparative Example 2 (about 5 mg each) were separately put in quartz pans and measured with the differential thermogravimetric analyzer (TG-DTA) TG8120 (product name, manufactured by Rigaku Corporation) at a temperature increase rate of 10° C./min, up to 600° C., placing alumina in each quartz pan as a reference.

As an indicator of heat resistance, a temperature at which a weight loss of 5% occurred ($T_{5\ wt\ \%}$) was calculated for each compound. The results are shown in Table 2.

TABLE 2

| | Heat resistance evaluation $T_{5\ wt\%}$ (° C.) |
|---|---|
| Example 2-1 | 306 |
| Example 2-2 | 295 |
| Example 2-3 | 308 |
| Example 2-4 | 295 |
| Example 2-5 | 300 |
| Example 2-6 | 310 |
| Example 2-7 | 309 |
| Example 2-8 | 308 |
| Example 2-9 | 302 |
| Comparative Example 2 | 279 |

[Conclusion]

From the results shown in Table 2, it was revealed that the compound of the disclosed embodiments of the present disclosure has significantly excellent heat resistance, which is a compound represented by the general formula (II) wherein the compound contains at least one of the following structures (i) and (ii):

(i) "A" is an aliphatic hydrocarbon group containing two or more alicyclic hydrocarbon groups, containing a saturated aliphatic hydrocarbon group at a terminal position directly bound to "N", and optionally containing O, S, N in a carbon chain.

(ii) At least one of $R^2$, $R^3$, $R^4$ and $R^5$ is a cycloalkyl group optionally containing a substituent group or an aryl group optionally containing a substituent group.

REFERENCE SIGNS LIST

1. Divalent or higher cation
2. Divalent or higher anion
3. Linking group "A"
4. Cationic moiety
10. Molecular association

The invention claimed is:

1. A compound represented by the following general formula (I):

General Formula (I)

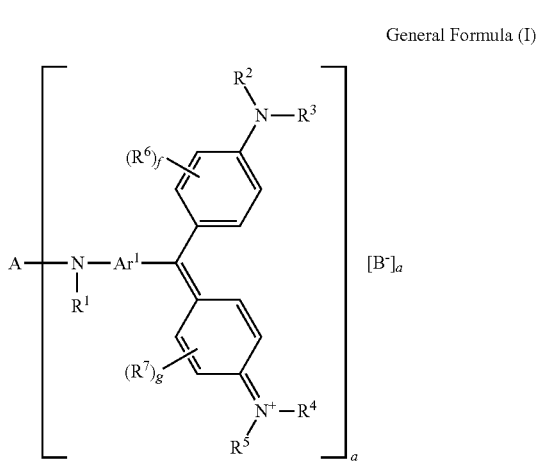

where:
"A" is a substituent group represented by the following general formula (V):

General Formula (V)

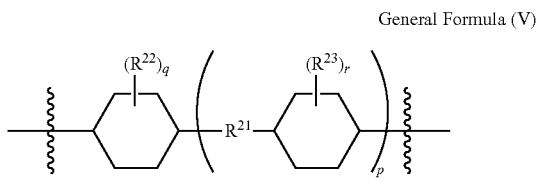

where $R^{21}$ is an alkylene group containing 1 to 3 carbon atoms and optionally containing, as a substituent group, an alkyl group containing 1 to 4 carbon atoms or an alkoxy group containing 1 to 4 carbon atoms; each of $R^{22}$ and $R^{23}$ is independently an alkyl group containing 1 to 4 carbon atoms or an alkoxy group containing 1 to 4 carbon atoms; "p" is an integer of from 1 to 3; each of "q" and "r" is independently an integer of from 0 to 4; when two or more $R^{21}$s are present, they may be the same or different; when two or more $R^{22}$s are present, they may be the same or different; when two or more $R^{23}$s are present, they may be the same or different; and when two or more "r"s are present, they may be the same or different;
each of $R^1$, $R^2$, $R^3$, $R^4$ and $R^5$ is independently a hydrogen atom, an alkyl group optionally containing a substituent group, or an aryl group optionally containing a substituent group; and $R^1$s may be the same or different, $R^2$s may be the same or different, $R^3$s may be the same or different, $R^4$s may be the same or different, and $R^5$s may be the same or different;
each of $R^6$ and $R^7$ is independently an alkyl group optionally containing a substituent group or an alkoxy group optionally containing a substituent group; and $R^6$s may be the same or different, and $R^7$s may be the same or different;
$Ar^1$ is a divalent aromatic group optionally containing a substituent group, and $Ar^1$s may be the same or different;
$B^-$ is a monovalent anion;
"a" is 2;
each "f" is independently an integer of from 0 to 4; and
each "g" is independently an integer of from 0 to 4.

2. A compound represented by the following general formula (II):

General Formula (II)

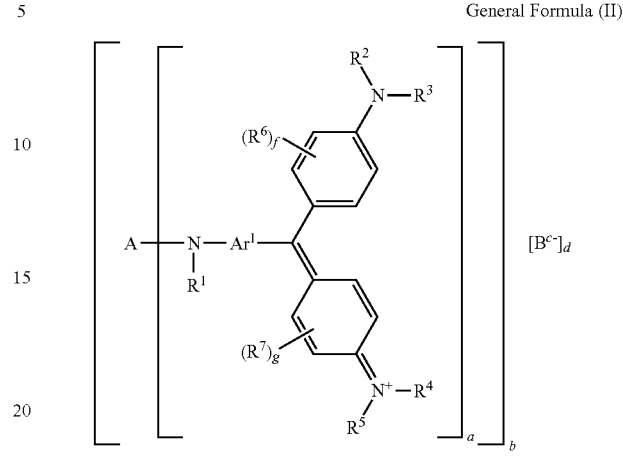

where:
"A" is a substituent group represented by the following general formula (V):

General Formula (V)

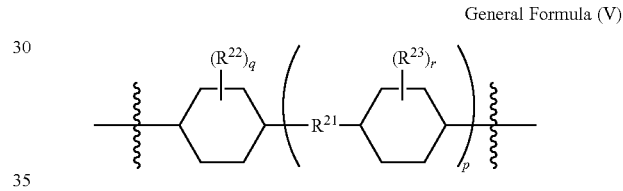

where $R^{21}$ is an alkylene group containing 1 to 3 carbon atoms and optionally containing, as a substituent group, an alkyl group containing 1 to 4 carbon atoms or an alkoxy group containing 1 to 4 carbon atoms; each of $R^{22}$ and $R^{23}$ is independently an alkyl group containing 1 to 4 carbon atoms or an alkoxy group containing 1 to 4 carbon atoms; "p" is an integer of from 1 to 3; each of "q" and "r" is independently an integer of from 0 to 4; when two or more $R^{21}$s are present, they may be the same or different; when two or more $R^{22}$s are present, they may be the same or different; when two or more $R^{23}$s are present, they may be the same or different; and when two or more "r"s are present, they may be the same or different;
each of $R^1$, $R^2$, $R^3$, $R^4$ and $R^5$ is independently a hydrogen atom, an alkyl group optionally containing a substituent group, or an aryl group optionally containing a substituent group; and $R^1$s may be the same or different, $R^e$s may be the same or different, $R^a$s may be the same or different, $R^4$s may be the same or different, and $R^5$s may be the same or different;
each of $R^6$ and $R^7$ is independently an alkyl group optionally containing a substituent group or an alkoxy group optionally containing a substituent group; and $R^6$s may be the same or different, and $R^7$s may be the same or different;
$Ar^1$ is a divalent aromatic group optionally containing a substituent group, and $Ar^1$s may be the same or different;
$B^{c-}$ is a "c"-valent anion;
"a" is 2;

"c" is an integer of 2 or more;
each of "b" and "d" is an integer of 1 or more;
each "f" is independently an integer of from 0 to 4;
each "g" is independently an integer of from 0 to 4.

3. The compound according to claim 1, wherein at least one of $R^2$, $R^3$, $R^4$ and $R^5$ is a cycloalkyl group optionally containing a substituent group or an aryl group optionally containing a substituent group.

4. The compound according to claim 1, wherein at least one of $R^2$, $R^3$, $R^4$ and $R^5$ is a substituent group represented by the following formula (III) or (IV):

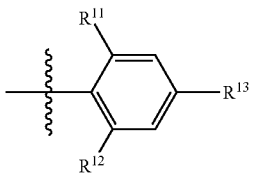

General Formula (III)

where each of $R^{11}$, $R^{12}$ and $R^{13}$ is independently a hydrogen atom, an alkyl group containing 1 to 4 carbon atoms and optionally containing a substituent group, or an alkoxy group containing 1 to 4 carbon atoms and optionally containing a substituent group,

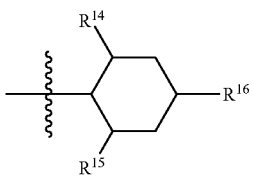

General Formula (IV)

where each of $R^{14}$, $R^{15}$ and $R^{16}$ is independently a hydrogen atom, an alkyl group containing 1 to 4 carbon atoms and optionally containing a substituent group, or an alkoxy group containing 1 to 4 carbon atoms and optionally containing a substituent group.

5. The compound according to claim 1, wherein $Ar^1$ is a divalent condensed polycyclic aromatic hydrocarbon group optionally containing a substituent group.

6. The compound according to claim 2, wherein the anion represented by $B^{c-}$ is a heteropolyoxometalate containing one or more elements selected from tungsten and molybdenum.

7. The compound according to claim 6, wherein at least one of $R^2$, $R^3$, $R^4$ and $R^5$ is a substituent group represented by the following formula (III) or (IV):

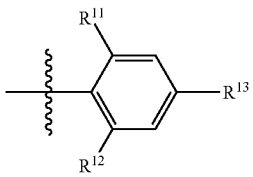

General Formula (III)

where each of $R^{11}$, $R^{12}$ and $R^{13}$ is independently a hydrogen atom, an alkyl group containing 1 to 4 carbon atoms and optionally containing a substituent group, or an alkoxy group containing 1 to 4 carbon atoms and optionally containing a substituent group,

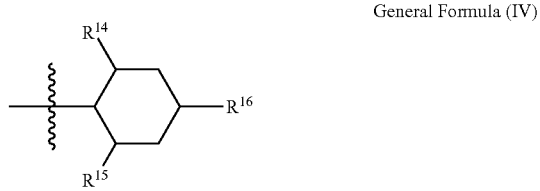

General Formula (IV)

where each of $R^{14}$, $R^{15}$ and $R^{16}$ is independently a hydrogen atom, an alkyl group containing 1 to 4 carbon atoms and optionally containing a substituent group, or an alkoxy group containing 1 to 4 carbon atoms and optionally containing a substituent group.

8. The compound according to claim 2, wherein at least one of $R^2$, $R^3$, $R^4$ and $R^5$ is a cycloalkyl group optionally containing a substituent group or an aryl group optionally containing a substituent group.

9. The compound according to claim 2, wherein at least one of $R^2$, $R^3$, $R^4$ and $R^5$ is a substituent group represented by the following formula (III) or (IV):

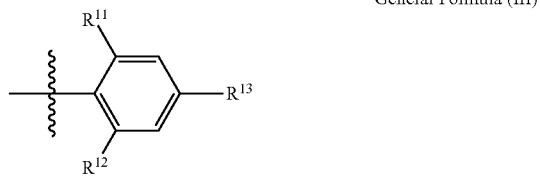

General Formula (III)

where each of $R^{11}$, $R^{12}$ and $R^{13}$ is independently a hydrogen atom, an alkyl group containing 1 to 4 carbon atoms and optionally containing a substituent group, or an alkoxy group containing 1 to 4 carbon atoms and optionally containing a substituent group,

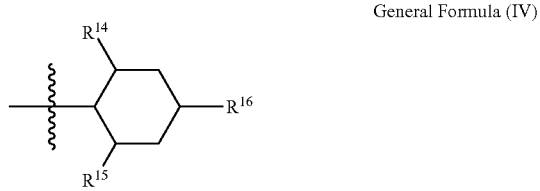

General Formula (IV)

where each of $R^{14}$, $R^{15}$ and $R^{16}$ is independently a hydrogen atom, an alkyl group containing 1 to 4 carbon atoms and optionally containing a substituent group, or an alkoxy group containing 1 to 4 carbon atoms and optionally containing a substituent group.

10. The compound according to claim 2, wherein $Ar^1$ is a divalent condensed polycyclic aromatic hydrocarbon group optionally containing a substituent group.

* * * * *